US006414018B1

(12) United States Patent
Duhaylongsod

(10) Patent No.: US 6,414,018 B1
(45) Date of Patent: *Jul. 2, 2002

(54) COMPOSITIONS, APPARATUS AND METHODS FOR FACILITATING SURGICAL PROCEDURES

(75) Inventor: Francis G. Duhaylongsod, Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/494,145

(22) Filed: Jan. 28, 2000

Related U.S. Application Data

(63) Continuation of application No. 09/131,075, filed on Aug. 7, 1998.
(60) Provisional application No. 60/055,127, filed on Aug. 8, 1997.

(51) Int. Cl.[7] ........................ A01N 47/00; A61N 1/18; A61N 1/20; A61N 1/22; A61N 1/28
(52) U.S. Cl. ...................... 514/478; 514/479; 514/922; 607/9; 607/10; 607/11; 607/16; 607/27; 607/28; 607/30; 600/16; 600/17; 600/18; 604/96; 604/272; 604/507; 604/508; 604/509; 604/510; 604/523; 604/532
(58) Field of Search ................................ 514/478, 479, 514/922; 607/9, 10, 11, 16, 27, 28, 30; 600/16, 17, 18; 604/507, 508, 509, 510, 96, 272, 523, 532

(56) References Cited

U.S. PATENT DOCUMENTS

| 3,241,556 A | 3/1966 | Zacouto |
| 3,640,269 A | 2/1972 | Delgado |
| 3,797,485 A | 3/1974 | Urquart |
| 4,162,679 A | 7/1979 | Reenstierna |
| 4,166,470 A | 9/1979 | Neumann |
| 4,230,119 A | 10/1980 | Blum |
| 4,248,214 A | 2/1981 | Hannah et al. |
| 4,309,776 A | 1/1982 | Berguer |
| 4,377,704 A | 3/1983 | Gero et al. |
| 4,404,971 A | 9/1983 | LeVeen et al. |
| 4,445,892 A | 5/1984 | Hussein et al. |
| 4,562,596 A | 1/1986 | Kornberg |
| 4,573,966 A | 3/1986 | Weikl et al. |
| 4,581,017 A | 4/1986 | Sahota |
| 4,605,399 A | 8/1986 | Weston et al. |
| 4,661,509 A | 4/1987 | Gordon et al. |
| 4,673,563 A | 6/1987 | Berne et al. |
| 4,736,024 A | 4/1988 | Della Valle et al. |
| 4,771,777 A | 9/1988 | Horewski et al. |
| 4,827,906 A | 5/1989 | Robicsek et al. |
| 4,857,552 A | 8/1989 | Rosenberg et al. |
| 4,923,457 A | 5/1990 | Ellingsen |
| 4,935,004 A | 6/1990 | Cruz |
| 4,962,095 A | 10/1990 | Grover et al. |
| 5,083,564 A | 1/1992 | Scherlag |
| 5,087,243 A | 2/1992 | Avitall |
| 5,095,903 A | 3/1992 | DeBellis |
| 5,096,929 A | 3/1992 | Chiesi et al. |
| 5,116,851 A | 5/1992 | Krapcho et al. |
| 5,124,326 A | 6/1992 | Mutschler et al. |
| 5,139,789 A | 8/1992 | Baumgarten |
| 5,152,277 A | 10/1992 | Honda et al. |
| 5,162,374 A | 11/1992 | Mulieri et al. |
| 5,176,638 A | 1/1993 | Michael |
| 5,182,102 A | 1/1993 | DeSantis, Jr. et al. |
| 5,229,127 A | 7/1993 | McKinzie |
| 5,287,861 A | 2/1994 | Wilk |
| 5,290,766 A | 3/1994 | Choong |

(List continued on next page.)

FOREIGN PATENT DOCUMENTS

| EP | 0 525 475 A2 | 2/1993 |
| EP | 0 525 475 A3 | 2/1993 |

(List continued on next page.)

OTHER PUBLICATIONS

"MIDCAB Technique" *Cardiac Surgery Renaissance,* The Advisory Board Company, Washington, D.C., pp. 108–111 (Jun. 1996).

(List continued on next page.)

*Primary Examiner*—Fredrick Krass
(74) *Attorney, Agent, or Firm*—Morrison & Foerster LLP

(57) ABSTRACT

Methods are provided for conducting surgical procedures in a patient wherein, during the surgical procedure, autonomous ventricular electrical conductivity and escape beats are reversibly and transiently suppressed to facilitate the surgical procedure. Also provided are compositions which are capable of inducing ventricular asystole in a patient. The compositions may include an AV node blocker. In one embodiment, compositions including an atrioventricular (AV) node blocker and a β-blocker are provided, wherein the β-blocker is present in an amount sufficient to substantially reduce the amount of AV node blocker required to induce ventricular asystole in the patient. The compositions and methods may be used for inducing temporary ventricular asystole in a beating heart, and to facilitate the performance of a variety of surgical techniques, including minimally invasive microsurgical techniques. Methods for performing a surgical procedure on a human patient are provided wherein a composition capable of inducing transient reversible ventricular asystole is administered to the heart, for example by intracoronary injection. The heart then is electrically paced using an electrical pacing system, thereby to maintain the patient's blood circulation. The electrical pacing then is selectively intermittently stopped to allow ventricular asystole to occur, and the steps of the surgical or therapeutic procedure, such as suturing, are conducted during the time that the electrical pacing is intermittently stopped. The methods and compositions advantageously may be used in a range of different surgical procedures including cardiac, vascular and neurosurgical procedures.

23 Claims, 8 Drawing Sheets

U.S. PATENT DOCUMENTS

| | | | |
|---|---|---|---|
| 5,312,344 A | 5/1994 | Grinfield et al. | |
| 5,320,604 A | 6/1994 | Walker et al. | |
| 5,356,427 A | 10/1994 | Miyata et al. | |
| 5,425,705 A | 6/1995 | Evard et al. | |
| 5,428,039 A | * 6/1995 | Cohen | 514/275 |
| 5,433,700 A | 7/1995 | Peters | |
| 5,442,053 A | 8/1995 | della Valle et al. | |
| 5,443,489 A | 8/1995 | Ben-Haim | |
| 5,452,733 A | 9/1995 | Sterman et al. | |
| 5,455,229 A | 10/1995 | Hahn et al. | |
| 5,458,574 A | 10/1995 | Machold et al. | |
| 5,459,140 A | 10/1995 | Gramer | |
| 5,474,783 A | 12/1995 | Miranda et al. | |
| 5,478,309 A | 12/1995 | Sweezer et al. | |
| 5,506,229 A | 4/1996 | Dow et al. | |
| 5,543,419 A | 8/1996 | Cross et al. | |
| 5,558,644 A | 9/1996 | Boyd et al. | |
| 5,591,195 A | 1/1997 | Taheri et al. | |
| 5,593,428 A | 1/1997 | Jamshidi | |
| 5,634,895 A | 6/1997 | Igo et al. | |
| 5,651,378 A | 7/1997 | Matheny et al. | |
| 5,735,290 A | 4/1998 | Sterman et al. | |
| 5,738,096 A | 4/1998 | Ben-Haim | |
| 5,873,366 A | 2/1999 | Chim et al. | |
| 5,913,876 A | 6/1999 | Taylor et al. | |

FOREIGN PATENT DOCUMENTS

| | | |
|---|---|---|
| EP | 0 528 776 A1 | 2/1993 |
| EP | 0 403 578 B1 | 10/1994 |
| EP | 0 664 104 A2 | 7/1995 |
| EP | 0 664 104 A3 | 7/1995 |
| EP | 0 783 902 A3 | 7/1997 |
| EP | 0 783 902 A2 | 7/1997 |
| EP | 0 791 332 A1 | 8/1997 |
| SU | 1731184 | 5/1992 |
| WO | WO 89/11855 | 12/1989 |
| WO | WO 94/18881 | 9/1994 |
| WO | WO 95/08364 | 3/1995 |
| WO | WO 95/10218 | 4/1995 |
| WO | WO 95/15192 | 6/1995 |
| WO | WO 95/15715 | 6/1995 |
| WO | WO 95/21573 | 8/1995 |
| WO | WO 95/35065 | 12/1995 |
| WO | WO 96/00033 | 1/1996 |
| WO | WO 96/05773 | 2/1996 |
| WO | WO 96/21489 | 7/1996 |
| WO | WO 97/25098 | 7/1997 |
| WO | WO 97/40885 | 11/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/16164 | 4/1998 |
| WO | WO 99/03533 | 1/1999 |

OTHER PUBLICATIONS

Acuff, T. E. et al., "Minimally invasive coronary artery bypass grafting" *Ann. Thorac. Surg.* 61:135–137 (1996).

Addetia et al., "Perfusion in cardioplegia: an experimental study" *Canadian J. Surg.* 23(2):146–150 (1980).

Agnarsson et al., "Carbachol depolarizes and accelerates pacemaker activity in the sinoatrial node of chicks treated with pertussis toxin" *J. Pharmacol. Exp. Ther.* 247(1):150–155 (1988).

American Hospital Formulary Service, "Miotics" *AHFS Drug Information* 52(20): 2167–2176 (1997).

Bachelard et al., "Regional haemodynamic effects of carbachol injected into the hypothalamic paraventricular nuclei of conscious, unrestrained rats" *Neuropharmacology* 33(6);769–788 (1994).

Bachman et al., "Different properties of the bradycardia produced by neostigmine and edrophonium in the cat" *Can. J. Anaeth.* 43(7):731–740 (1996).

Backman et al., "Mechanism of the bradycardia produced in the cat by the anticholinesterase neostigmine"*J. Pharmacol. Exp. Ther.* 265(1):194–200 (1993).

Backman et al., "Neostigmine decreases heart rate in heart transplant patients" *Can J. Anaesth.*43(4):373–378 (1996).

Badeer et al., "Factors affecting pulsus alternans in the rapidly driven heart and papillary muscle"*Am. J. Physiology* 213(5):1095–1101 (1967).

Baker, A. B. et al., "Intentional asystole during endoluminal thoracic aoritic surgery without cardiopulmonary bypass" *Br. J. Anaesth.* 78:444–448 (1997).

Beal, "Changes in renal haemodynamics and electrolyte excretion after intraventricular infusion of carbachol in conscious sheep" *Quarterly Journal of Experimental Physiology* 65:159–171 (1980).

Bel et al., "Inhibition of the pacemaker current: a bradycardic therapy for off–pump coronary operations" *Ann. Thorac. Surg.* 66:148–52 (1998).

Belardinelli et al., "Evidence for adenosine mediation of atrioventricular block in the ischemic canine myocardium" *J. Clin. Invest.* 68(1):195–205 (1981).

Benetti, F.J. and Ballester, C., "Use of thoracoscopy and a minimal thoracotomy, in mammary–coronary bypass to left anterior descending artery, without extracorporeal circulation" *J. Cardiovasc. Surg.* 36:159–161 (1995).

Benetti, F.J. et al., "Video assisted coronary bypass surgery" *J. Card. Surg.* 10:620–625 (1995).

Bjork et al., "Coronary angiography during acetylcholine–induced cardiac arrest" *Acta. Soc. Med. Upsal.* 71:253–262 (1966).

Bjork et al., "Coronary angiography during acetylcholine–induced cardiac arrest in patients with angina pectoris" *The J. Cardiovascular Surgery* 2(1):9–19 (1961).

Broadley, "The release of a coronary vasodilator metabolite from the guinea–pig isolated perfused heart stimulated by catecholamines, histamine and electrical pacing and by exposure to anoxio" *Br. J. Pharmac.* 58:89–100 (1976).

Broadley, K.J. and Rothaul, A.L., "Catecholamine–induced vasodilator metabolite release from guinea–pig hearts is not due to increased myocardial activity" *Pflügers Arch.* 391;147–153 (1981).

Brockman et al., "Experimental open heart surgery employing hypothermia, mecholyl arrest, and carotid perfusion" *Surgery* 43:815–823 (1958).

Buffolo et al., "Coronary artery bypass grafting without cardiopulmonary bypass" *Ann. Thorac. Surg.* 61:63–66 (1996).

Bufkin et al., "Controlled intermittent asystole for non-–pump cardiac surgery: Pharmacologic potentation of vagal-–induced asystole" Conference Abstract (Jan. 1998).

Burger et al., "Prevention of urinary retention after general surgery: A controlled trial of carbachol/diazepam versus alfusozine" *J. Am. Coll. Surg.* 185:234–236 (1997).

Calafiore, A.M. et al., "Left anterior descending coronary artery grafting via left anterior small thoracotomy without cardiopulmonary bypass"*Ann. Thorac. Surg.* 61:1658–1665 (1996).

Carbachol (definition). Source: http://www.rxmed.com/monographs/carba2.html (Aug. 6, 1997).

Chiba et al., "Differences in chronotropic and dromotropic responses of the SA and AV nodes to adenosine and acetylcholine" *SHORT COMMUNICATIONS Japan J. Pharmacol.* 22:273–274 (1972).

Chiba et al., "Blocking of acetylcholine–induced fibrillation by use of norepinephrine into the AV node artery" *The Japanese Journal of Physiology* 20:560–570 (1970).

Chiba et al., "Effect of bethanechol, methacholine and carbachol on AV conduction of the dog heart" *Jap. Heart J.* 13(4):347–353 (1972).

Chiba et al., "Interruption of atrial fibrillation by pacemaker shift induced by the selective use of noradrenaline into the A–V node artery" *Tohok J. exp. Med.* 95:411–413 (1968).

Chinet et al., "Comparison of the dose–response curves obtained by forced oscillation and plethysmography during carbachol inhalation" *Eur. Respir. J.* 1:600–605 (1988).

Cooley, D.A., "Limited access myocardial revascularization" *Tex. Heart Inst. J.* 23(2):81–84 (1996).

Dorros et al., "Adenosine–induced transient cardiac asystole enhances precise deployment of stentin the thoracic or abdominal aorta" *Endovasc. Surg.* 3:270–272 (1996).

Dotter et al., "Coronary arteriography during induced cardiac arrest and aortic occlusion" *AMA Arch. Internal Med.* 104(1):58/720–67/729 (1959).

Ede, M. et al., "Beyond hyperkalemia: β–blocker–induced cardiac arrest for normothermic cardiac operations" *Ann. Thoracic Surg.* 63:721–727 (1997).

Emmerson et al., "The zig–zag tracheal strip" *J. Pharm. Pharmacol.* 31:798 (1979).

Gundy, S.R. et al., "Coronary artery bypass with and without the heart–lung machine: A Case Matched 6 year Followup" *American Heart Assoc., 69th Scientific Sessions,* Atlanta, GA, p. I–52, Abstract No. 293 (Nov. 10–13, 1996).

Guntheroth et al., "Alternate deletion and potentiation as the cause of pulsus alternans" *Am. Heart J.* 78(5):669–681 (1969).

Guvendik et al., "Oral–beta–blockade with hypothermic potassium cardioplegia in cardiac surgery: is there an additive protective effect?" *Thorac. Cardiovasc. Surg.* 34:25–29 (1986).

Hedlund et al., "Effects of prazosin and carbachol in patients with benign prostatic obstruction" *Scand. J. Urol. Nephrol.* 22:19–22 (1988).

Hesselvik et al., "The use of neostigmine to decrease the heart rate in a patient undergoing minimally invasive coronary artery bypass surgery" *J. of Cardiothorac. and Vascular Anesthesis* 11(7):883–884 (1997).

Hua et al., "Alpha$_{1A}$– and alpha$_{1a}$–adrenoreceptor–mediated positive chronotropic effects on isolation rat atrium" *Acta Pharmacologica Sinica* 14(4):317–319 (1993).

Kanter et al., "Beneficial effects of adding propranolol to multidose potassium cardioplegia" *Circulation* 64(21 Pt 2):1184–1190 (1981).

Kihara et al., "abnormal $Ca_1^{2+}$ handling is the primary cause of mechanical alternans: Study in ferret ventricular muscles" *Am. J. Physiol.* 261(6 Pt 2):H1746–H1755 (1991).

Koglin et al., "Antiadrenergic effect of carbachol but not of adenosine on contractility in the intact human ventricle in vivo" *J. Am. Coll. Cardiol.* 23(3):678–683 (1994).

Lam et al., "Experiences in the Use of Cardioplegia (Induced Cardiac Arrest) in the Repair of Interventricular Septal Defects" *J. Thoracic Surg.* 34:509–520 (1957).

Lam, C.R. et al., "Acetylcholine–induced asystole. An adjunct in open heart operations with extracorporeal circulation" *Extracorporeal Circulation,* (J.G. Allen et al., Eds.), Charles C. Thomas, Springfield, IL, pp. 451–458 (1958).

Lam, C.R. et al., "Clinical Experiences with induced cardiac arrest during intracardiac surgical procedures" *Ann. Surg.* 146:439–449 (1957).

Lam, C.R. et al., "Induced cardiac arrest (cardioplegia) in open heart surgical procedures" *Surgery* 43:7–13 (1958).

Lam, C.R. et al., "Induced cardiac arrest for intracardiac surgical procedures" *J. Thorac. Surg.* 30:620–625 (1955).

Lang et al., "Stimulation of sudomotor axon reflex mechanism by carbachol in healthy subjects and patients suffering from diabetic plyneuropathy" *Acta Neurologica Scandinavica* 91:251–254 (1995).

Khanna, R. and Cullen, H.C., "Coronary artery surgery with induced temporary asystole and intermittent ventricular pacing: An experimental study" *Cardiovasc. Surg.* 4(2):231–236 (1996).

Larach, D.R. "Cardiovascular Drugs" *The Practice of Cardiac Anesthesia,* F.A. Hensley Jr. and D.E. Martin (eds.), Little, Brown and Company: Cardiology Roundtable interviews, pp. 108–111 (1990).

Lillehei et al., "Clinical experience with retrograde perfusion of the coronary sinus for direct vision aortic valve surgery with observations upon use of elective asystole or temporary coronary ischemia" *Extracorporeal Circulation,* (J.G. Allen et al., Eds.), Charles C. Thomas, Springfield, IL, pp. 466–485 (1958).

Lillehei et al., "The direct vision correction of calcific aortic stenosis by means of a pump–oxygenator and retrograde coronary sinus perfusion" *Diseases of the Chest* 30(2):123–132 (1956).

Lillehei et al., "The surgical treatment of stenotic or regurgitant lesions of the mitral and aortic valves by direct vision utilizing a pump–oxygenator" *J. Thoracic Surg.* 35:154–191 (1958).

Lin et al., "Warm blood cardioplegia (WBC) prevents dysfunction of endothelium–dependent relaxation (EDR) and endothelium–dependent contraction (EDC) of coronary artery after global ischemia & reperfusion (IR)" American Heart Association., *Abstracts From the 69th Scientific Sessions,* New Orleans, LA, Abstract (Nov. 10–13, 1996).

Martin et al., "Mechanisms of the cardiovascular response to posterior hypothalamic nucleus administration of carbachol" *J. Cardiovasc. Pharmacol.* 27:891–900 (1996).

Matheny et al., "Vagus nerve stimulation as a method to temporarily slow or arrest the heart" *Ann. Thorac. Surg.* 63:S28–9 (1997).

Mondini et al., "Pharmacologic arrest of the heart in experimental animals" *J. Intl. Coll. Surgeons* 28(1):20–29 (1957).

Nayler, W.G. and Robertson, P.G.C., "Mechanical alternans and the staircase phenomenon in dog papillary muscle" *Am. Heart J.* 70(4):494–498 (1965).

Nelson et al., "Discussions" *Extracorporeal Circulation,* Thomas, Charles, C., Springfield, IL, pp. 486–491 (1958).

Noble R.J. et al., "The demonstration of alternating contractile state in pulsus alternans." *J. Clin. Invest* 49:1166–1177 (1970).

Philp et al., "Drug effects on the voiding cystometrogram: a comparison of oral bethanecol and carbachol" *British Journal of Urology* 52:484–487 (1980).

*Physicians' Desk Reference or Ophthalmology*, Medical Economics Co., Montvale, NJ, 25th edition, pp. 10–11, 221–223 (1997).

*Physicians' Desk Reference*, Medical Economics Co., Montvale, NJ, 50th edition, pp. 2728–2730 (1996).

Pick et al., "Third and Fourth operations for myocardial ischemia short–term results and long–term survival" American Heart Assoc., *Abstracts From the 69th Scientific Sessions*, New Orleans, LA, Abstract (Nov. 10–13, 1996).

Lyte B.W., "Minimally invasive cardiac surgery" *J. Thorac. Cardiovasc. Surg.*III:554–555 (1996).

Otorii, T., "Effects of Beta–adrenoreceptor blocking agents on the deslanoside–induced arrhythmia and cardiac arrest in guinea pigs" *Japanese Circ. J.*35:1535–1540 (1971).

Porlier et al., "The effects of acetylstrophanthidin on the response of the AV junction to adrenergic stimulation studied in dogs" *American Heart Journal* 91(4):475–483 (1976).

Rials et al., "Effects of atropine on the cardiac arrest induced by propranolol and digitoxin in dogs" *J. Electrocardiology* 15(3):277–284 (1982).

Rivetti et al., "Initial experience using an intraluminal shunt during revascularization of the beating heart" *Ann. Thorac. Surg.* 63:1742–1747 (1997).

Robinson et al., "Transient ventricular asystole using adenosine during minimally invasive and open sternotomy coronary artery bypass grafting" *Ann. Thoracic Surg.* 63:S30–S34 (1997).

Ruiz et al., "Effects of carbachol and acetylcholine on intraocular pressure after cateract extraction" *Am J. Ophthalmol.* 107(1):7–10 (1989).

Sangster et al., "Two cases of carbachol intoxication" *Neth J. Med.* 22:27–8 (1979).

Schaff, H.V. et al., "Minimal thoracotomy for coronary artery bypass: Value of immediate postprocedure graft angiography" American Heart Assoc., *Abstracts From the 69th Scientific Sessions*, New Orleans, LA, Abstract (Nov. 10–13, 1996).

Schwartz, D.A., "Surgery for Acquired Heart Disease" *J. Thorac, Cardiovasc. Surg.* 111(3):556–566 (1996).

Sealy, W.C. et al., "Potassium, Magnesium, and Neostigmine for Controlled Cardioplegia" *J. Thoracic Surg.* 37:655–659 (1959).

Sergeant et al., "Further studies in induced cardiac arrest using the agent acetylcholine" *The Heart* pp. 254–257 (1997).

Schumaker, "Induced cardiac arrest, coronary perfusion, deep hypothermia, and circulatory arrest" The Evolution of Cardiac Surgery, Ch. 32, Indiana University Press, pp. 280–292, 432–437 (1992).

Stevens, J.H. et al., "Port–access coronary artery bypass with cardioplegic arrest: Acute and chronic canine studies" *Ann. Thorac. Surg.* 62:435–441 (1996).

Takeda et al., "Effects on atrio–ventricular conduction of alinidine and falipamil injected into the AV node artery of the anesthetized dog", *Arch int. Pharmacodyn.* 297:39–48 (1989).

Takeuchi et al., "Superior myocardial protection with histidine buffered crystalloid cardioplegia versus blood: A clinical trial" American Heart Association., *Abstracts from the 69th Scientific Sessions*, New Orleans, LA, Abstract (Nov. 10–13, 1996).

The Royal Pharmaceutical Society, "Evaluated information on the world's drugs and medicines" Martindale: The extra Pharmacopoeia, 31st edition, pp. 1418–1419 (1996).

Ullyot, D.J., "Look ma, no hands!" *Ann. Thorac. Surg.* 61:10–11 (1996).

USPDI, "Advice for the patient: Drug information in lay language", 17th edition, vol. 2, pp. 442–443 (1997).

USPDI, "Drug information for the health care professional", 17th edition, vol. 1, pp. 712–713 (1997).

Viljoen et al., "Propanolol and cardiac surgery" *The J. of Thoracic and Cardiovascular Surgery* 64(5):826–830 (1972).

von der Burchard et al., "A comparison between drug–induced cardioplegia and hypothermia on myocardial protection during ischemia" *Pflügers archiv.* 382(suppl):R3 Abstract No. 11 (1979).

von der Burchard et al., "The effect of different kinds of drug–induced cardioplegia on myocardial protection during oxygen lack in normo– and hypothermia" *Arch. Pharmcol.* 311(suppl):R34 Abstract No. 134 (1980).

Wohlfart, B., "Analysis of mechanical alternans in rabbit papillary muscle" *Acta Physiol Scand.* 115:405–414 (1982).

Preusse et al., "Post–ischemic mhocardialfunction after pre–ischemic appplication of propranolol or verapamil" *J. Cardiovasc. Surg.*25:158–164 (1984).

Stevens, J.H. et al., "Port–access coronary artery bypass grafteing: Aproposed surgical method" *J. Thorac. Cardiovasc. Surg.*111:567–573 (1996).

Thielmeier, K.A. et al., "Role of ademosine–induced ventricular asystole during minimally invasive CABG: Optimizing the surgical field" *Anesthesiology*85(3A):A162 Abstract (1996).

\* cited by examiner

COMPOSITIONS, APPARATUS AND METHODS FOR FACILITATING SURGICAL PROCEDURES

CROSS REFERENCE TO RELATED APPLICATIONS

This application is a continuation of U.S. patent application Ser. No. 09/131,075, filed Aug. 7, 1998, which claims the benefit of U.S. Provisional Application Ser. No. 60/055,127, filed Aug. 8, 1997, the disclosures of which are incorporated herein by reference.

TECHNICAL FIELD

The present invention relates to compositions and methods that facilitate the performance of medical and surgical procedures, such as cardiac surgical procedures, including minimally invasive coronary bypass surgery.

BACKGROUND ART

Heart attacks and angina pectoris (chest pain) are caused by occlusions in the coronary arteries. Atherosclerosis, the major cause of coronary artery occlusions, is characterized by deposits of fatty substances, cholesterol, calcium and fibrin within the arterial wall. As the coronary arteries narrow, blood flow is reduced depriving the heart of much needed oxygen. This occurrence is called myocardial ischemia. Severe and prolonged myocardial ischemia produces irreparable damage to the heart muscle, pronounced cardiac dysfunction, and possibly death. Apart from medical therapy, atherosclerosis is treated with coronary artery bypass graft surgery (CABG), percutaneous transluminal coronary angioplasty (PTCA), stents, atherectomy, and transmyocardial laser revascularization (TMLR).

In patients where PTCA, stents, and atherectomy are unsuitable or unsuccessful, CABG is the procedure of choice. In the conventional CABG operation, a long vertical incision is made in the chest, the sternum is split longitudinally and the halves are spread apart to provide access to the heart. Two large bore tubes, or cannulas, are then inserted directly into the right atrium and the aorta in order to establish cardiopulmonary bypass (CPB). The aorta is occluded with an external clamp placed proximal to the aortic cannula. A third cannula is inserted proximal to the aortic clamp, and is used for the delivery of a cardioplegic solution into the coronary arteries. The hyperkalemic cardioplegic solution protects the heart by stopping atrial and ventricular contraction, thereby reducing its metabolic demand. When the heart is not beating, blood flow to the rest of the body is provided by means of CPB. Cardiopulmonary bypass involves removing deoxygenated blood through the cannula in the right atrium, infusing the blood with oxygen, and then returning it through the cannula in the aorta to the patient. With the heart motionless, the surgeon augments blood flow to the ischemic heart muscle by redirecting blood around the coronary artery occlusion. Although there are several methods to bypass an occlusion, the most important method involves using the left internal thoracic artery (LITA). The LITA normally originates from the left subclavian artery and courses along the anterior chest wall just lateral of the sternum. For this operation, the LITA is mobilized from the chest wall and, with its proximal origin left intact, the distal end is divided and sewn to the coronary artery beyond the site of occlusion (most commonly the left anterior descending coronary artery). After the LITA anastomosis is completed and any further arterial or vein grafts are completed, CPB is weaned as the heart resumes its normal rhythm. The cannulae are removed, temporary pacing wires are sewn to the heart, and plastic tubes are passed through the chest wall and positioned near the heart to drain any residual fluid collection. The two halves of the sternum are approximated using steel wire.

Because the traditional method of performing CABG involves significant operative trauma and morbidity to the patient, attention has been directed to developing less invasive surgical techniques that avoid splitting the sternum. The new techniques are performed with or without CPB through smaller incisions placed between the ribs. One method, called port-access, utilizes groin cannulation to establish CPB, while another, called minimally invasive direct coronary artery bypass or MIDCAB, is performed on the beating heart and therefore does not require CPB. Insofar as these techniques succeed in achieving less operative trauma compared to conventional CABG, postoperative pain is improved, the length of hospitalization is shortened, and the return to normal activity is hastened. The port-access approach avoids the sternal splitting incision by employing femoral venoarterial CPB and an intraaortic (endoaortic) balloon catheter that functions as an aortic clamp by means of an expandable balloon at its distal end (Daniel S. Schwartz et al. "Minimally Invasive Cardiopulmonary Bypass With Cardioplegic Arrest: A Closed Chest Technique With Equivalent Myocardial Protection." *Journal of Thoracic & Cardiovascular Surgery* 1996; 111:556–566. John H. Stevens et al. "Port-Access Coronary Artery Bypass Grafting: A Proposed Method." *Journal of Thoracic & Cardiovascular Surgery* 1996; 111:567–573. John H. Stevens et al. "Port-Access Coronary Artery Bypass With Cardioplegic Arrest: Acute and Chronic Canine Studies." *Annals of Thoracic Surgery* 1996; 62:435–41). This catheter also includes a separate lumen for the delivery of cardioplegic solution and venting of the aortic root. Alternatively, a different catheter may be placed percutaneously into the internal jugular vein and positioned in the coronary sinus for delivery of retrograde cardioplegic solution. Coronary bypass grafting is performed through a separate limited left anterior thoracotomy incision with dissection of the LITA and anastomosis to the atherosclerotic coronary artery under direct vision. Other bypass grafts to coronary arteries can be accomplished using radial artery sewn to the LITA. A description of port-access procedures is found in U.S. Pat. No. 5,452,733, the complete disclosure of which is incorporated herein by reference. Thus, the port-access approach focuses on avoiding the sternal splitting incision while maintaining a motionless heart to facilitate a precise coronary anastomosis as the primary means to reduce operative trauma and morbidity. Compelling evidence to support this contention, however, is scarce. Furthermore, no evidence exists regarding the effectiveness of the coronary anastomosis performed through the limited incision, nor the safety of the intraaortic balloon clamp and the vascular sequelae of groin cannulation. Finally, the port-access approach does not avoid the damaging effects of cardiopulmonary bypass, which include: 1) a systemic inflammatory response; 2) interstitial pulmonary edema; 3) neuropsychological impairment; 4) acute renal insufficiency; and 5) nonmechanical microvascular hemorrhage.

The MIDCAB approach also avoids the sternal splitting incision, favoring instead a limited left anterior thoracotomy incision (Tea E. Acuffet al. "Minimally Invasive Coronary Artery Bypass Grafting." *Annals of Thoracic Surgery* 1996; 61:135–7. Federico J. Benetti and Carlos Ballester, "Use Of Thoracoscopy And A Minimal Thoracotomy, In Mammary-Coronary Bypass To Left Anterior Descending Artery, Without Extracorporeal Circulation." *Journal of Cardiovascular Surgery* 1995; 36:159–61. Federico J. Benetti et al. "Video Assisted Coronary Bypass Surgery." *Journal of Cardiac Surgery* 1995; 10:620–625). Similarly, dissection of the LITA and anastomosis to the coronary artery are then performed under direct vision. The principal difference between the MIDCAB and port-access techniques, however, involves the utilization of cardioplegic solution and CPB (Denton A. Cooley, "Limited Access Myocardial Revascularization" *Texas Heart Institute Journal* 1996; 23:81–84; and Antonio M. Calafiore et al., "Left Anterior Descending Coronary Artery Grafting via Left Anterior Small Thoracotomy without Cardiopulmonary Bypass," *Annals of Thoracic Surgery* 1996; 61:1658–65). Because MIDCAB is performed on the beating heart, cardioplegic solution, aortic cross-clamping and CPB are not required. This approach therefore focuses on the avoidance of cardiopulmonary bypass, aortic cross-clamping and the sternal splitting incision as the primary means to reduce operative trauma and morbidity after conventional CABG.

The potential advantages of MIDCAB compared to conventional CABG include: 1) the avoidance of CPB and aortic cross-clamping; 2) fewer embolic strokes; 3) less blood loss, hence a decreased transfusion requirement; 4) fewer perioperative supraventricular arrhythmias; 5) earlier separation from mechanical ventilatory support; 6) decreased or eliminated intensive care unit stay; 7) shorter length of hospitalization; 8) reduced total convalescence with earlier return to preoperative activity level; and 9) lower overall cost. Despite these potential benefits, however, the durability of the LITA to coronary artery anastomosis is uncertain. At the recent American Heart Association 69th Annual Scientific Session, the Mayo Clinic group reported on 15 patients undergoing MIDCAB. Of these 15 patients, three or 20% required reoperation to revise the anastomosis during the same hospitalization (Hartzell V. Schaff et al., "Minimal Thoracotomy For Coronary Artery Bypass: Value Of Immediate Postprocedure Graft Angiography," Abstract presented at the American Heart Association, 69th Scientific Sessions, Nov. 10–13, 1996, Atlanta, Ga.). Of greater significance, however, was a report from Loma Linda University Medical Center that demonstrated a seven-year LITA to left anterior descending coronary artery patency rate of 42% in a subset of patients who underwent beating heart surgery and presented with recurrent angina. In contrast, the patency rate in an age-, sex- and disease severity-matched control group was 92% (Steven R. Gundry et al., "Coronary Artery Bypass with and Without the Heart-Lung Machine: A Case Matched 6-year Follow-up," Abstract presented at the *American Heart Association, 69th Scientific Sessions*, Nov. 10–13, 1996, Atlanta, Ga.). Finally, because the MIDCAB approach is restricted mostly to patients with isolated disease of the left anterior descending coronary artery, the vast majority of patients with atherosclerotic heart disease are not appropriate candidates. Thus, despite the potential benefits of MIDCAB, its safety, efficacy, and applicability remain uncertain.

There are major obstacles to precise coronary anastomosis during MIDCAB. The constant translational motion of the heart and bleeding from the opening in the coronary artery hinder precise suture placement in the often tiny coronary vessel. Although bleeding can be reduced by using proximal and distal coronary occluders, by excluding diagonal and septal branches near the arterial opening when possible, and by continuous saline irrigation or humidified carbon dioxide insufflation, the incessant motion of the beating heart remains the Achilles' heel of minimally invasive coronary artery bypass.

In summary, although port-access and minimally invasive direct coronary artery bypass techniques avoid the operative trauma and morbidity associated with the sternal splitting incision, both have serious disadvantages. The port-access approach is encumbered by the morbidity of cardiopulmonary bypass and aortic cross-clamping and the cost of the apparatus. Furthermore, the safety of the intraaortic balloon clamp and the vascular sequelae of groin cannulation are unresolved issues. The MIDCAB approach is imperiled by the constant motion of the beating heart which precludes a precise coronary anastomosis. Reports of poor graft patency rates and the need for early reoperation in a significant proportion of patients after MIDCAB attests to the technical difficulty of the procedure.

Conventional CABG requires arrest of the heart through the use of cardioplegic agents, aortic cross-clamping and cardiopulmonary bypass. These cardioplegic agents stop the beating heart to thereby allow precise suture placement and other surgical procedures. A mixture of magnesium sulfate, potassium citrate, and neostigmine has been used to induce cardioplegia during cardiopulmonary bypass. Sealy et al. "Potassium, Magnesium, And Neostigmine For Controlled Cardioplegia: A Report Of Its Use In 34 Patients," *Journal of Thoracic Surgery* 1959, 37:655–59. Although both magnesium and potassium remain integral components of modern cardioplegic solutions, neostigmine was ultimately eliminated. Potassium citrate is currently the most commonly used cardioplegic agent. Potassium impedes excitation-contraction coupling, however, making it impossible to pace the heart by electrical stimulation and necessitating the use of a cardiopulmonary bypass system to sustain the patient. Other chemical agents that have been used in human cardiac operations to slow the rate of ventricular contraction include acetylcholine, neostigmine, adenosine, lignocaine, and esmolol. Another agent, carbachol or carbamyl choline, has been used to induce cardiac arrest in experimental animals. Broadley and Rothaul, *Pflugers Arch.*, 391:147–153 (1981).

Acetylcholine has been used as a cardioplegic agent during cardiopulmonary bypass. Lam et al., "Induced Cardiac Arrest In Intracardiac Procedures, An Experimental Study," *Journal of Thoracic Surgery* 1955; 30:620–25; Lam et al., "Clinical Experiences With Induced Cardiac Arrest During Intracardiac Surgical Procedures," *Annals of Surgery* 1957; 146:439–49; Lam et al., "Induced Cardiac Arrest (Cardioplegia) In Open Heart Procedures," *Surgery* 1958; 43:7–13; and Lam et al., "Acetylcholine-induced Asystole. An adjunct In Open Heart Operations With Extracorporeal Circulation," in *Extracorporeal Circulation* 1958, pp. 451–48; Lillehei et al., "The Direct Vision Correction Of Calcific Aortic Stenosis By Means Of A Pump Oxygenator And Retrograde Coronary Sinus Perfilsion," *Disease Of The Chest*, 1956, 30:123–132; Lillehei et al., "Clinical Experience With Retrograde Perftision Of The Coronary Sinus For Direct Vision Aortic Valve Surgery With Observations Upon Use of Elective Asystole Or Temporary Coronary Ischemia," in *Extracorporeal Circulation*, 1958, pp. 466–85; Lillehei et al., "The Surgical Treatment Of Stenotic Or Regurgitant Lesions Of The Mitral And Aortic Valves By Direct Vision Utilizing A Pump Oxygenator," *Journal of Thoracic & Cardiovascular Surgery*, 1958; 35:154–91. Conrad R. Lam, et al. *Annals of Surgery* 1957; 146:439–49. Intravenous adenosine has been used to facilitate MIDCAB. M. Clive Robinson, *First International Live Teleconference. Least-Invasive Coronary Surgery*, The John Radcliffe Hospital, Oxford, England, Mar. 21 and 22, 1996.

Ventricular asystole has been achieved by direct injection of lignocaine into the interventricular septum. Khanna and Cullen, "Coronary Artery Surgery With Induced Temporary Asystole And Intermittent Ventricular Pacing: An Experimental Study," *Cardiovascular Surgery* 1996; 4(2):231–236. Epicardial pacing wires were placed, and ventricular pacing was employed to maintain an adequate cardiac output. Esmolol has been used as a cardioplegic agent during cardiopulmonary bypass. Mauricio Ede et al., "Beyond Hyperkalemia: Beta-Blocker-Induced Cardiac Arrest For Normothermic Cardiac Operations," *Annals of Thoracic Surgery*, 1997; 63:721–727.

In summary, there is a need for a surgical approach that avoids the risks and costs of cardiopulmonary bypass while preserving the benefits of a motionless operative field to achieve a precise coronary anastomosis. There is a further need for methods and compositions that enable predictable, controllable, transient arrest of the heart, which stop or slow the beating heart with acceptable half-life and quick onset of effect. There is a need for compositions and methods for transient arrest of the heart which can be used in a variety of surgical procedures conducted on the heart, vascular system, brain, or other major organs, where pulsatile flow, movement associated with arterial pulsations, or bleeding is undesirable during the procedure.

SUMMARY OF THE INVENTION

Methods, compositions and apparatus are provided which are useful for medical and surgical therapeutic applications. The methods and compositions are useful for cardiac surgery and other procedures, such as neurosurgery and vascular surgery, which require precise control of cardiac contraction. Other applications include non-invasive procedures such as percutaneous aortic aneurysm graft placement, and invasive procedures such as brain surgery. Using the methods and compositions disclosed herein for conducting a surgical procedure, such as a coronary bypass, a substantially motionless operative field is provided.

In one aspect, there is provided a method of inducing reversible ventricular asystole in a beating heart in a human patient, the method comprising administering a compound and a β-blocker to the heart of the patient in an amount effective to induce ventricular asystole, while maintaining the ability of the heart to be electrically paced, wherein the β-blocker is administered in amount sufficient to substantially reduce the amount of compound required to induce ventricular asystole. In one embodiment, the compound may be an atrioventricular (AV) node blocker. The β-blocker may be administered in an amount sufficient to reduce the amount of AV node blocker, which is required to induce ventricular asystole, to, for example, about 50% or less by weight of the amount of AV node blocker alone required to induce ventricular asystole. The compound may be a cholinergic receptor agonist, such as carbachol. The cholinergic receptor agonist, such as carbachol, may be administered in an amount, for example, of about 0.1 to 4.8 µg/kg body weight/min. The β-blocker, may be, for example, propranolol. The propranolol may be administered, for example, in an amount of about 0.01 to 0.07 mg/kg body weight. In one embodiment, the β-blocker is propranolol and the AV node blocker is carbachol, and the propranolol is administered prior to or during administration of the carbachol. The propranolol and the carbachol may be administered, for example, to the coronary artery of the patient.

In another embodiment, there is provided a method of inducing reversible ventricular asystole in a beating heart in a human patient, the method comprising administering a cholinergic receptor agonist and a β-blocker to the heart of the patient in an amount effective to induce ventricular asystole, wherein the amount administered of the cholinergic receptor agonist alone or the β-blocker alone is not sufficient to induce ventricular asystole.

In another embodiment, there is provided a method of conducting a surgical procedure on a human patient comprising: administering a β-blocker and an AV node blocker to the heart of a human patient to induce reversible ventricular asystole while maintaining the ability of the heart to be electrically paced; electrically pacing the heart with an electrical pacing system; selectively intermittently stopping the electrical pacing to allow ventricular asystole; and conducting the surgical procedure during the time that the electrical pacing is intermittently stopped. In one embodiment, the β-blocker is administered prior to the AV node blocker. The AV node blocker may be a cholinergic agent, such as carbachol. The β-blocker may be administered in an amount sufficient to substantially reduce the amount of AV node blocker required to induce ventricular asystole. The surgical procedure may be, for example, a cardiac surgical procedure. In one embodiment, the electrical pacing is selectively intermittently interrupted by a surgeon conducting the surgical procedure by selectively manipulating a control that is functionally coupled to the electrical pacing system. The β-blocker and the cholinergic agent may be administered, for example, sequentially or simultaneously, and may be administered, for example, to the right or left coronary artery, left ventricle, the aorta, the right ventricle, the pulmonary artery, the pulmonary vein, or the coronary sinus. The cholinergic receptor agonist, such as carbachol, may be administered, for example, in an amount of about 0.1 to 4.8 µg/kg body weight/min. The β-blocker, may be, for example, propranolol, which may be administered, for example, in an amount of about 0.01 to 0.07 mg/kg body weight. In one embodiment, the β-blocker is propranolol and the AV node blocker is carbachol, and the propranolol is administered prior to or during administration of the carbachol.

In one embodiment, the propranolol is administered by a single bolus injection in the right or left coronary artery, prior to the administration of carbachol, and the carbachol is administered by a single bolus injection followed by continuous infusion into the right or left coronary artery to maintain the ventricular asystole. Surgical procedures that may be conducted include minimally invasive coronary bypass procedures, neurological procedures and endovascular procedures. Other surgical procedures include treatment of injuries to the liver, spleen, heart, lungs, and major blood vessels, as well as electrophysiologic procedures and cardiac surgery with or without cardiopulmonary bypass.

In another embodiment, there is provided a method of inducing reversible ventricular asystole in a human patient comprising administering carbachol to the heart of the patient. The carbachol may be administered, for example, to the coronary sinus, or may be administered intraventricularly, or to the aortic root or coronary artery of the patient. Optionally, propranolol also may be administered to the heart of the patient. The propranolol may be administered, for example, prior to or during the administration of the carbachol.

In a further embodiment, there is provided a method of inducing reversible ventricular asystole in the heart of a human patient comprising administering carbachol to the patient at a dosage of about 1 to 15 mg, for example, about 1 to 12 mg. In another embodiment, there is provided a method of inducing reversible ventricular asystole in the heart of a human patient, the method comprising administering carbachol to the patient at a rate of 0.1 to 4.8 µg/kg body weight/min.

In another embodiment, there is provided a method of inducing reversible ventricular asystole in the heart of a human patient, the method comprising: administering an initial intracoronary bolus of carbachol of about 0.1 to 10 µg/kg body weight of the patient; and administering a continuous intracoronary infusion of carbachol at a rate of about 0.1–4.8 µg/kg body weight/min. The initial intracoronary bolus of carbachol is administered, for example, over about 1–5 minutes. The intracoronary infusion of carbachol is administered, for example, over a time period of about 5 to 120 minutes. The initial intracoronary bolus may comprise, for example about 0.1 to 5 µg carbachol/kg body weight, and may be provided in a suitable pharmaceutically acceptable carrier.

In a further embodiment, there is provided a method of inducing reversible ventricular asystole in a human patient comprising: administering an intracoronary bolus injection of about 0.01 to 0.5 mg of carbachol over about 0.5 to 3 minutes; and administering an intracoronary infusion of carbachol at a rate of about 0.01 to 0.3 mg/min over about 30 to 90 minutes.

In a further embodiment, there is provided a method of inducing reversible ventricular asystole of a heart of a human patient while maintaining the ability of the heart to be electrically paced comprising: administering at least a first compound to the heart of the patient which is capable of inducing third-degree AV block of the heart; and administering at least a second compound to the heart of the patient which alone or in combination with the first compound is capable of substantially suppressing ectopic ventricular beats in the heart while maintaining the ability of the heart to be electrically paced.

In another embodiment, there is provided a method of inducing reversible ventricular asystole in the heart of a patient, while maintaining the ability of the heart to be electrically paced comprising: administering an AV-node blocker and a compound to the heart of the patient in an amount effective to induce ventricular asystole, while maintaining the ability of the heart to be electrically paced, wherein the compound is administered in an amount sufficient to reduce the amount of AV-node blocker required to induce ventricular asystole.

In a further embodiment, a method of performing a surgical procedure on a human patient is provided, the method comprising: administering an effective amount of a composition capable of inducing reversible ventricular asystole to the patient, while maintaining the ability of the heart to be electrically paced; electrically pacing the heart with an electrical pacing system, thereby to maintain the patient's blood circulation; selectively intermittently stopping the electrical pacing to allow ventricular asystole; and conducting the surgical procedure during the time that the electrical pacing is intermittently stopped. The composition capable of inducing ventricular asystole may comprise, in one embodiment, an atrioventricular (AV) node blocker. The composition may further comprise a β-blocker, wherein the β-blocker is present in an amount sufficient to substantially reduce the amount of AV node blocker required to induce ventricular asystole. In another embodiment, the composition may comprise a cholinergic agent and a β-blocker, wherein the amount by weight administered of either the cholinergic agent alone or the β-blocker alone is not sufficient to induce complete heart block and suppression of ventricular escape beats, but in combination, due to a synergistic effect, is effective to induce ventricular asystole.

According to another aspect of the invention, a cardiac surgical procedure is conducted by inducing reversible ventricular asystole in the heart of a human patient without cardiopulmonary bypass, and/or without aortic cross-clamping.

According to another aspect, a composition is provided that is capable of inducing reversible ventricular asystole in a patient, while maintaining the ability of the heart to be electrically paced. The composition may include an atrioventricular (AV) node blocker. In one embodiment, the composition may include a compound capable of inducing reversible ventricular asystole in a patient and a β-blocker in an amount sufficient to substantially reduce the amount of the compound required to induce ventricular asystole in the patient. The composition may include, for example, an atrioventricular (AV) node blocker, such as carbachol and a β-blocker, such as propranolol. The β-blocker is provided in one embodiment in an amount sufficient to substantially reduce the amount of AV node blocker required to induce ventricular asystole. For example, the AV node blocker may be present in the composition in an amount which is 50% or less by weight, or optionally about 1 to 20 % by weight of the amount of AV node blocker alone required to induce ventricular asystole. The composition may comprise, for example carbachol in a pharmaceutically acceptable solution at a dosage amount of about 1 to 20 mg. The composition may include propranolol in a pharmaceutically acceptable carrier in a dosage form for administration to a patient in an amount of about 0.01 to 0.07 mg/kg body weight of the patient. In one embodiment, the composition may comprise propranolol present in a pharmaceutically acceptable solution at a dosage amount of about 1 to 10 mg. Methods are provided for administering an effective amount of the compositions to a patient to induce reversible ventricular asystole during a surgical procedure.

In another embodiment, a composition is provided which is capable of inducing ventricular asystole in a patient, while maintaining the ability of the heart to be electrically paced, comprising a cholinergic receptor agonist and a β-blocker. In one embodiment, the amount of either the cholinergic receptor agonist alone or the β-blocker alone in the composition is not sufficient to induce ventricular asystole in the patient.

In another embodiment, a sterile dosage form of carbachol is provided, which may be provided in form suitable for use in a surgical procedure. The dosage form of carbachol may be in a pharmaceutically acceptable form for parenteral administration, for example to the cardiovascular system, or directly to the heart, such as by intracoronary infusion. The carbachol may be provided in a variety of pharmaceutically acceptable carriers. In one embodiment, a sterile dosage form of carbachol is provided comprising about 1–20 mg of carbachol in a pharmaceutically acceptable carrier. Carriers include aqueous solutions including saline, aqueous solutions including dextrose, water and buffered aqueous solutions.

In yet another embodiment, the invention provides the use of a β-blocker in the manufacture of a medicament for use in conjunction with a compound capable of inducing reversible ventricular asystole in the heart of a patient, for use in a method of inducing transient reversible ventricular asystole in the heart of a patient, while maintaining the ability of the heart be electrically paced, the amount of β-blocker being sufficient to reduce substantially the amount of the compound required to induce ventricular asystole.

There is further provided the use of a compound capable of inducing reversible ventricular asystole in the manufacture of a medicament for use in conjunction with a β-blocker for use in a method of inducing transient reversible ventricular asystole in the heart of a patient, while maintaining the ability of the heart be electrically paced, the amount of β-blocker being sufficient to reduce substantially the amount of the compound required to induce ventricular asystole.

In another embodiment, there is provided the use of a β-blocker in the manufacture of a medicament for use in conjunction with a cholinergic receptor agonist, for use in a method of inducing transient reversible ventricular asystole in the heart of a patient, while maintaining the ability of the heart to be electrically paced, the amount of the cholinergic receptor agonist administered alone or the β-blocker administered alone not being sufficient to induce ventricular asystole in the heart of the patient.

In another aspect, there is provided the use of a cholinergic receptor agonist in the manufacture of a medicament for use in conjunction with a β-blocker, for use in a method of inducing transient reversible ventricular asystole in the heart of a patient, while maintaining the ability of the heart to be electrically paced, the amount of cholinergic receptor agonist administered alone or the β-blocker administered alone not being sufficient to induce ventricular asystole in the heart of the patient.

According to another aspect of the invention, a patient may be prepared for coronary artery bypass by placing at least a portion of a delivery device in a coronary vessel of the patient's heart and delivering a cardioplegic agent to the AV node of the patient via the coronary vessel with the device, which may be a catheter, for example. In one embodiment, the device is placed in the right coronary artery of the heart of the patient. In another embodiment, it is placed in the left coronary artery of the heart of the patient. The device may include an outlet and the outlet placed in the right coronary artery of the heart of the patient and immediately proximal to the AV node artery. In another embodiment, the device outlet may be placed in the AV node artery. In further embodiments, the device may be placed in the middle cardiac vein of the heart of the patient or in an ostium of a right or left coronary artery of the heart of the patient. In another embodiment, the device may be introduced through the femoral artery. The device also may be introduced through an incision in the aorta of the patient.

According to another aspect of the invention, a kit is provided comprising one or more agents capable of inducing ventricular asystole. For example, the kit may include separate containers of an AV node blocker and a β-blocker. In one embodiment, the kit is provided with a first container comprising a dosage amount of a cholinergic receptor agonist and a second container comprising a dosage amount of a β-blocker. Dosage amounts of cholinergic receptor agonist and β-blocker may be included that are suitable for simultaneous, separate or sequential use in a surgical procedure for inducing transient reversible ventricular asystole in a patient. In one embodiment, the cholinergic receptor agonist is carbachol and the β-blocker is propranolol. The carbachol and/or propranolol may be in a pharmaceutically acceptable carrier. According to one embodiment, the first container contains about 1 to 20 mg of carbachol, and the second container contains about 1 to 10 mg of propranolol. Other possible components of the kit include pacing electrodes, drug delivery devices and catheters. The electrodes may be, for example, epicardial or endocardial pacing electrodes. Other components of the kit can include pacing catheters and devices, and coronary perfusion catheters and devices, catheter introducers, a pump system and/or tubes, or other surgical devices. The drug delivery device may be in various forms including a catheter, such as a drug delivery catheter or guide catheter, a cannula or a syringe and needle assembly. The drug delivery catheter may include an expandable member, and a shaft having a distal portion, wherein the expandable member is disposed along the distal portion. The expandable member may be a low-pressure balloon. The kit may be in packaged combination, such as in a pouch, bag or the like. The kit may further include instructions for the use of components of the kit in a surgical procedure, such as instructions for use of compounds to induce transient reversible ventricular asystole in the heart of a patient undergoing a surgical procedure.

According to another aspect of the invention, a pacing system is provided comprising an extracorporeal pacer for delivering pacing signals to a human heart, a switch coupled to the pacer, and a switch actuator arranged remote from the pacer. The remote actuator may enhance procedure control when used, for example, during a surgical procedure. The pacing system may include pacing leads coupled to the switch and adapted for coupling to the heart of the patient. The switch may be remote from the pacer. The actuator may be remote from the switch. Further, the actuator may take various forms. For example, in one embodiment, the actuator may comprise a foot pedal and in another, it may comprise a needle holder. An actuator override circuit also may be provided as well as indicators indicating various states of pacing.

The above is a brief description of some deficiencies in the prior art and advantages of the present invention. Other features, advantages and embodiments of the invention will be apparent to those skilled in the art from the following description, accompanying drawings and appended claims.

DETAILED DESCRIPTION

Figure 1:
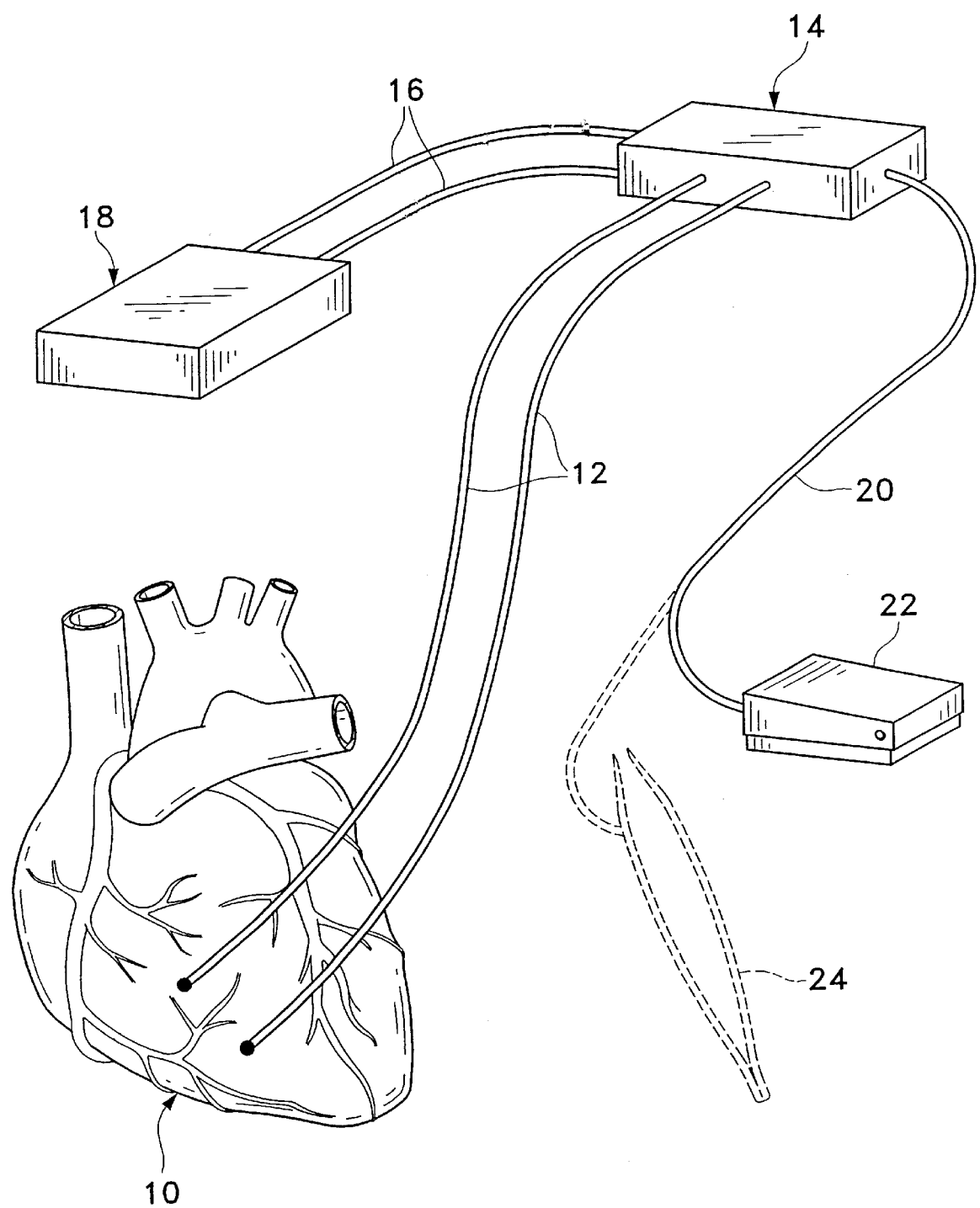
FIG. 1 diagramatically shows a pacing system in accordance with the principles of the invention.

Compositions and methods are provided which are useful for medical and surgical therapeutic applications. The compositions and methods are useful for cardiac surgery and other procedures such as neurosurgery and vascular surgery which require precise control of cardiac contraction. In one embodiment, the compositions and methods are useful for coronary artery bypass procedures, with or without cardiopulmonary bypass. Using the methods and compositions for conducting a coronary artery bypass disclosed herein, a motionless operative field is provided.

The methods and compositions of the invention are useful for any procedure which requires controlled temporary complete heart block and suppression of ventricular escape beats. Examples of such procedures include coronary bypass surgery (with full or partial sternotomy or thoracotomy), transmyocardial laser revascularization, tachyarrhythmia operations such as electrophysiology lab procedures (diagnostic and therapeutic ablation of arrhythmias), imaging procedures of the heart and great vessels such as CAT scan or MRI procedures, percutaneous transluminal coronary angioplasty, placement of stents such as coronary or aortic stents, operations where uncontrollable hemorrhage is present or anticipated or control of significant hemorrhage is required during the surgical procedure (for example, treatment of injuries to the liver, spleen, heart, lungs, or major blood vessels, including iatrogenic and traumatic injuries to such organs or structures), other procedures including percutaneous aortic aneurysm graft placement, and neurosurgical procedures, such as aneurysm repair. The methods and compositions are useful for any surgical procedure or intervention on the heart, vascular system, brain, or other major organs, where pulsatile flow, movement associated with arterial pulsations, or bleeding prevents successful completion of the operative procedure.

The compositions and methods can be used to induce ventricular asystole in a patient, for example, prior to a surgical procedure. The term "ventricular asystole" as used herein refers to a state wherein autonomous electrical conduction and escape rhythms in the ventricle are suppressed. Preferably, a state of the heart is induced wherein the heart beats less than about 25 beats per minute, for example, less than about 12 beats per minute. The induced ventricular asystole is reversible and after reversal, the heart functions are restored, and the heart is capable of continuing autonomous function. Preferred are pharmaceutically acceptable compositions which are capable of inducing transient reversible ventricular asystole reliably and predictably.

The compositions capable of suppressing autonomous ventrical electrical conduction and escape rhythms may in one embodiment comprise an atrioventricular (AV) node blocker. As used herein, the term "AV node blocker" refers to a compound capable of reversibly suppressing autonomous electrical conduction at the AV node, while still allowing the heart to be electrically paced to maintain cardiac output. Preferably, the AV node blocker, or composition comprising the AV node blocker, reduces or blocks ventricular escape beats and cardiac impulse transmission at the AV node of the heart, while the effect on depolarization of the pacemaker cells of the heart is minimal or nonexistent. The AV node blocker preferably induces third degree, or complete AV block, or significantly slows AV conduction to the point where the ventricular beat is less than about 25 beats per minute, for example less than about 12 beats per minute. The AV node blocker, or composition comprising the AV node blocker, preferably induces reversible ventricular asystole, and renders the heart totally pacemaker dependent for a limited period of time, such that a pacemaker may be used to maintain pacing and to intermittently stop pacing during a surgical step. After the surgical procedure is completed, for example, less than about 2 hours, the heart then can be returned to its normal intrinsic rhythm.

Exemplary AV node blockers include calcium channel blockers, adenosine A1 receptor agonists, adenosine deaminase inhibitors, cholinesterase inhibitors, monoamine oxidase inhibitors, serotoninergic agonists, antiarrythmics, cardiac glycosides, local anesthetics and combinations thereof. Examples of AV node blockers include adenosine, digoxin, digitalis, procaine, lidocaine, procainamide, quinidine, verapamil, chloroquine, amiodarone, ethmozine, propafenone, flecainide, encainide, pilocarpine, diltiazem, dipyridamole, ibutilide, zapranest, sotalol and metoclopromide and combinations thereof. AV node blocking also can be achieved by other methods including direct electrical stimulation, vagal nerve stimulation, stimulation with ultrasonic energy, and temporary cooling of the AV node using a cryonic agent. Cryonic agents include devices, such as cryostats, and cryogenic chemicals which are capable of inducing low temperatures at the AV node.

The AV node blocker, capable of causing ventricular asystole, in a preferred embodiment is a cholinergic agent. As used herein, the term "cholinergic agent" refers to a cholinergic receptor modulator, which is preferably an agonist. The cholinergic agent in a preferred embodiment is carbachol (carbamyl choline chloride). Other cholinergic agents which may be used include any naturally occurring cholinergic (acetylcholine) receptor agonists or synthetic derivatives. Exemplary cholinergic agents include acetylcholine, methacholine, bethanechol, arecoline, norarecoline, pyridostigmine, neostigmine, and other agents that increase cyclic GMP levels by direct or indirect receptor stimulation.

In one embodiment, compositions and methods are provided which are capable of slowing or preventing autonomous conduction of electrical impulses from the sinoatrial node to the ventricle, with suppression of escape beats in the AV node and the ventricle. Preferably, a state of the heart is induced wherein the heart beats less than about 25 beats per minute, for example, less than about 12 beats per minute.

As used herein, the term "β-adrenergic blocking agent," also referred to as a "β-blocker", is defined as an agent which is capable of blocking β-adrenergic receptor sites. In a preferred embodiment, the β-blocker is propranolol. Other β-blockers which can be used include atenolol, acebutolol, labetalol, metoprolol, nadolol, oxprenolol, penbutolol, pindolol, sotalol and timolol. Other exemplary β-blockers include celiprolol, betaxolol, bevantolol, bisoprolol, esmolol, alprenolol, carterolol, nadolol or teratolol, and mixtures thereof. The β-blocker may be any naturally occurring or synthetic analogue capable of blocking β-adrenergic receptor sites.

In one embodiment, reversible ventricular asystole in a beating heart in a human patient is induced by administering to a patient a composition capable of suppressing autonomous ventricular electrical conduction and escape rhythms. In one embodiment, the composition capable of inducing ventricular asystole may comprise a first compound capable of inducing ventricular asystole, such as an AV node blocker, and a β-blocker present in an amount sufficient to substantially reduce the amount of the compound required to induce ventricular asystole. In one embodiment, the combination of the compound, such as an AV node blocker together with the β-blocker provides a synergistic effect such that the amount of AV node blocker required to induce reversible ventricular asystole may be reduced in comparison to the amount of AV node blocker required alone. Methods also are provided wherein the β-blocker is administered either prior to or contemporaneously with the compound capable of inducing ventricular asystole, in an amount effective to substantially reduce the amount of the compound required to be administered to induce ventricular asystole.

In a particular embodiment, ventricular asystole is induced in a beating heart in a human patient by administering a cholinergic receptor agonist and a β-blocker to the heart of the patient in an effective amount to induce ventricular asystole, wherein the amount administered of the cholinergic receptor agonist alone or the β-blocker alone is not sufficient to induce ventricular asystole. In one embodiment, the co-administration of the β-blocker with the cholinergic agent provides a synergistic effect, such that the amount of cholinergic agent which is administered to induce reversible ventricular asystole can be reduced.

Reversible ventricular asystole in the heart of a human patient thus may be induced by administration of an AV node blocker, or mixture of AV node blockers, to the heart of the patient. Reversible ventricular asystole optionally is induced by administration of the combination of an AV node blocker, such as a cholinergic agent, and one or more β-blockers to the heart of the patient. The β-blocker is preferably administered either prior to or contemporaneously with the AV node blocker.

In an embodiment wherein a surgical procedure is to be conducted, after inducing reversible ventricular asystole, the method further includes electrically pacing the heart with an electrical pacing system, thereby to maintain the patients blood circulation; selectively intermittently stopping the electrical pacing to allow ventricular asystole; and conducting the surgical procedure during the intervals of time that the electrical pacing is intermittently stopped.

The method may be used, for example, in a cardiac surgical procedure. Electrical pacing may be controlled by a surgeon conducting the surgical procedure by selectively manipulating a control that is functionally coupled to the electrical pacing system. Once reversible ventricular asystole is achieved, pacing of the heart may be implemented using a external pacemaker connected to the heart, and the pacemaker may be periodically deactuated, for example by way of a foot switch, to allow reversible ventricular asystole, thereby facilitating the performance of coronary artery bypass, with or without cardiopulmonary bypass, or other procedures elsewhere in the body of the patient.

For example, to conduct a coronary artery bypass, the patient's heart is provided with ventricular pacing electrodes connected to an electrical pacing device, which is controlled by the surgeon. A composition, for example, comprising an AV node blocker and a β-blocker, then is administered to the patient to induce reversible ventricular asystole. The surgeon then employs the pacing device to pace the heart and sustain the patient's circulation. The surgeon intermittently stops the electrical pacing for a few seconds to place a single suture, and re-starts it after each successive suture, thus permitting a precise coronary anastomosis to be performed. In this method, the ventricles (and/or atria) are electrically paced and maintain a normal cardiac output except for the brief periods of time that are required to accurately place a single suture in the coronary artery, preferably about 2 to 15 seconds, and more preferably about 2 to 5 seconds. Using the methods and compositions described herein, the rate and timing of ventricular contraction can be directly controlled.

In the method, the composition inducing ventricular asystole, such as an AV node blocker in combination with a β-blocker or AV node blocker administered after a β-blocker, may be infused through a catheter placed into the right coronary artery.

In one embodiment, the composition is delivered locally to the AV node of the heart upon which it acts via the AV node artery of the heart. Preferably the composition is delivered to the right coronary artery which feeds blood to the AV node artery. In a majority of patients, the right coronary artery is the main vessel supplying blood to the right side of the heart and to the AV node. However, where the right coronary artery is substantially totally occluded, and in a small subset of about 20% of patients, the first septal branch of the left anterior descending artery which originates from the left coronary artery may be the vessel which delivers blood to the AV node and can be selected as the delivery conduit for delivering the composition to the AV node. Additionally, other possible routes of administration to the AV node may include Kugel's artery and the right superior descending artery. Preferably, the composition is delivered to the right coronary artery or left coronary artery at a location near the bifurcation to the AV node artery and proximal to the right coronary artery's bifurcation into the posterior descending artery by any one of a number of drug delivery means, such as a drug delivery catheter suitably positioned within the right coronary artery. Other methods of administration may be used including hypodermic needle injection into, for example, any of the vessels noted above which may supply blood to the AV node, such as the right coronary artery or the first septal branch. Other methods of administration include needle injection into the aorta, needle injection directly into the AV node artery or the AV node itself, a transepicardial absorption pad, i e., a myocardial patch which slowly releases the composition directly into the heart's myocardium, and for example, an intraoperative cannula or other similar guide introducer or sheath which can be surgically placed by a surgeon into the aorta or the ostium of a coronary vessel without the need for X-ray fluoroscopy.

As the composition achieves the desired effect of ventricular asystole, the ventricle is electrically paced to maintain a stable rhythm and blood pressure. To interrupt the electrical pacing of the heart, the surgeon uses a convenient control means, such as a foot pedal or hand held actuator, as shown in FIG. 1, and is thereby able to stop the heart as sutures are placed in the coronary arterial wall. Because the heart is motionless during the critical period as the surgeon places sutures, precision and safety are enhanced. The time required to place a single suture into the coronary artery preferably does not exceed 15 seconds, and is preferably about 2 to 5 seconds, most preferably about 2 to 4 seconds. Thus, the compositions can permit the elimination of the translational motion of the beating heart.

Compositions capable of inducing ventricular asystole in a patient are provided which in one embodiment include a cholinergic receptor agonist and a β-blocker, wherein the amount of the cholinergic receptor agonist alone or the β-blocker alone in the composition is not sufficient to induce ventricular asystole in the patient. Methods are provided wherein the cholinergic receptor agonist and the β-blocker may be administered, either sequentially or together, thereby to induce ventricular asystole in a patient, wherein the amount of the cholinergic receptor agonist administered alone or the β-blocker administered alone is not sufficient to induce ventricular asystole in the patient.

In one embodiment, wherein a cholinergic agent and a β-blocker are administered to the heart of a human patient to induce reversible ventricular asystole, when the β-blocker used is propranolol and the cholinergic receptor agonist used is carbachol, a continuous infusion rate of about 0.1 to 4.8 μg/kg/min of carbachol can be used, e.g, an infusion rate of carbachol of 0.1 to 2.1 μg/kg/min, or about 0.1 to 1.5 μg/kg/min, or in one preferred embodiment, about 1.5 to 2.1 μg/kg/min. When an initial bolus of propranolol is administered prior to or during administration of an initial bolus of carbachol, the ratio by weight of propranolol to carbachol in the bolus injections can range, for example, from about 1:2 to 35:1, or, in another embodiment, from about 1:1 to 15:1, or, in another embodiment, from about 2:1 to 10:1, or, in another embodiment, is about 5:1.

In another embodiment, compositions capable of inducing ventricular asystole in a patient are provided, comprising a compound, such as an atrioventricular (AV) node blocker, and a β-blocker, wherein the β-blocker is present in an amount sufficient to substantially reduce the amount of the compound required to induce ventricular asystole in the patient. The AV node blocker is preferably a cholinergic agent. Due to the synergistic effect of the presence of the β-blocker, the cholinergic agent may be present in the composition in a reduced amount which is, for example, about 1–90%, about 1–50%, or about 1–20%, or for example, about 2–14%, or in another embodiment about 80% or less, for example about 50% or less, or about 10% or less by weight of the amount of the cholinergic agent alone required to induce ventricular asystole in the patient. Advantageously, the co-administration of the β-blocker with the AV node blocker provides a synergistic effect, such that the amount of AV node blocker which is administered to induce ventricular asystole may be reduced.

Additionally, in the methods disclosed herein, ventricular asystole may be induced in a patient by administration, together, or sequentially, of a compound, such as an AV node blocker, together with a β-blocker, wherein the β-blocker is administered in an amount sufficient to substantially reduce the amount of the compound required to induce ventricular asystole in the patient. In a preferred embodiment, the compound is a cholinergic agent, such as carbachol. Due to the synergistic effect of the administration of the β-blocker, the cholinergic agent may be administered in reduced amount which is, for example, about 1–90%, about 1–50%, or about 1–20%, or in one embodiment, about 2–14%, or in another embodiment about 80% or less, about 50% or less, or about 10% or less by weight of the amount of the cholinergic agent alone required to induce ventricular asystole in the patient.

Additionally, due to the synergistic effect, the β-blocker may be present in combination with other compounds capable of inducing ventricular asystole, in an amount effective to reduce the amount of the compound required to induce ventricular asystole, for example to about 5–90%, e.g., 30–50% or less by weight of the amount alone required to induce ventricular asystole.

The administration of the β-blocker is preferably prior to, or contemporaneously with, the administration of the cholinergic agent, and in one embodiment results in a synergistic effect between the β-blocker and the cholinergic agent. The amount of β-blocker present is preferably not sufficient to induce ventricular asystole by itself, and is sufficient only to cause a local β-blockade, but has a minimal effect on electrical conduction of the heart, or is low enough to cause only a first degree heart block.

In another embodiment, in order to induce reversible ventricular asystole in the heart of a patient, while maintaining the ability of the heart to be electrically paced, an AV node blocker is administered in combination with an effective amount of a second compound, such as a β-blocker to reduce or suppress ectopic ventricular activity while maintaining the ability of the heart to be electrically paced. In one embodiment, the β-blocker, alone or in combination with the AV node blocker, is capable of substantially suppressing ectopic ventricular beats in the heart while maintaining the ability of the heart to be electrically paced. For example, an AV node blocker, such as an antiarrythmic, such as flecainide, and a β-blocker, such as propranolol, may be administered. In one preferred embodiment, the β-blocker is administered prior to the AV node blocker. In another embodiment, a composition is provided that includes an AV node blocker and a β-blocker in an amount effective to induce reversible ventricular asystole and wherein the β-blocker is present in an amount effective to reduce or suppress ectopic ventricular activity after administration.

The use of a cholinergic agent, such as carbachol, in combination with a β-blocker, such as propranolol, preferably produces ventricular asystole at significantly reduced dosages of the cholinergic agent, while maintaining a short half-life and rapid onset of effect. A preferred half-life is on the order of about one to ten minutes. A preferred onset of effect is less than one minute after administration. It is possible to induce onset of ventricular asystole within about thirty seconds after administration of carbachol and propranolol to the heart.

The compositions preferably are capable of inducing reversible transient ventricular asystole of a beating heart to facilitate the performance of minimally invasive surgical procedures, while still permitting the heart to be electrically paced. The compositions, including for example a cholinergic agent, preferably can reliably and in a dose-dependent fashion produce extended periods of reversible ventricular asystole, for example, for up to about two hours upon either administration of a single dose, or continuous infusion, depending upon the composition. In preferred embodiments, the ventricular asystole is chemically reversible. For example, in the case of carbachol, the ventricular asystole can be reversed by administering atropine, for example by an intravenous bolus injection, providing an important advantage of safety during the procedure.

In one preferred embodiment, to induce ventricular asystole, the β-blocker is administered to the heart before the cholinergic agent For example, the β-blocker in one embodiment is administered in a single bolus injection into the right or left coronary artery, and then the cholinergic agent is administered by a single bolus injection followed by continuous infusion into the right or left coronary artery throughout the surgical procedure, to maintain the ventricular asystole. In another embodiment, where the β-blocker has a relatively short half life, such as esmolal, the β-blocker may be administered by continuous infusion, or a plurality of bolus infusions. The ventricular asystole continues as long as administration of the cholinergic agent is continued In a preferred embodiment, due to the prior administration of the β-blocker, it is possible to administer a significantly reduced amount of the cholinergic agent and thereby reduce the occurrence of side-effects such as systemic hypotension. Moreover, depolarization of the pacemaker cells of the heart by the administered composition is preserved, thereby making it possible to selectively electrically pace the heart to permit the performance of a surgical procedure while the heart is under transient ventricular asystole.

The time between administration of the β-blocker and the cholinergic agent is preferably long enough to permit the β-blocker to cause a local β-blockade of the pacemaker cells of the heart. After bolus administration, the time interval can be, for example about two minutes. In the case of intravenous or other forms of administration, several minutes or even hours may be required to permit the β-blocker to affect the pacemaker cells of the heart. The subsequent administration of the cholinergic agent may be controlled by the surgeon. Bolus infusion of higher doses can be used to give a dose dependent effect, while continuous infusion of lower doses also may be given to maintain ventricular asystole. In another embodiment, the β-blocker may be administered by an initial intracoronary bolus followed by a continuous infusion.

In one embodiment, the AV node blocker, such as a cholinergic agent, such as carbachol, is administered in an initial intracoronary bolus of about 0.1 to 150 µg/kg body weight of patient, or about 2 to 20 µg/kg body weight of patient, for example, about 4 to 16 µg/kg, or about 6 to 14 µg/kg, or in one embodiment, about 8 to 12 µg/kg body weight, in a suitable pharmaceutically acceptable carrier. The AV node blocker, such as carbachol, is preferably administered over a time period of about 0.1 to 3 minutes, preferably about 0.5 to 1 minute. In a preferred embodiment, the AV node blocker, such as a cholinergic agent, such as carbachol, is administered in an intracoronary bolus of about 0.10 to 10 µg/kg body weight of patient, for example about 0.10 to 5.0 µg/kg body weight in a pharmaceutically acceptable carrier over a time period of about 0.1 to 3 minutes, preferably about 0.5 to 1 minute.

The bolus infusion of the AV node blocker such as a cholinergic agent is in one embodiment followed by a continuous intracoronary infusion at about 0.1–5 µg/kg body weight/min of the AV node blocker, which in a preferred embodiment is a cholinergic agent. The infusion rate in one embodiment is about 0.14.8 µg/kg body weight of patient/min, for example about 0.1–2.1 µg/kg/min, or about 0.1–1.5 µg/kg/min, or about 0.1–1.0 µg/kg/min, or in another embodiment, about 0.1–0.5 µg/kg/min. Optionally, the cholinergic agent is combined with a β-blocker. In one embodiment, a typical total adult dosage of an AV node blocker, such as a cholinergic agent, such as carbachol, is about 1 mg to 15 mg. This dosage can produce reversible ventricular asystole, for example, for a time period of about 5 to 120 minutes, for example, about 5 to 90 minutes, preferably about 30 to 90 minutes, e.g., about 75 minutes. The dosage may also be, for example, about 1 to 12 mg, or about 1 to 10 mg, or in one embodiment about 1 to 5 mg. The dosage may be adjusted depending on the surgical procedure.

The β-blocker, such as propranolol, in one embodiment is administered through the right or left coronary artery in a dosage of about 0.01 to 0.07 mg/kg body weight of patient, for example, 0.01 to 0.05 mg/kg, or about 0.01 to 0.04 mg/kg. The total amount of propranolol administered is in one embodiment about 1 mg to 6 mg, e.g., about 1 mg to 5 mg, or, for example, about 2 to 4 mg, or about 3 mg.

For example, one embodiment to induce transient reversible ventricular asystole in a patient is as follows. An intracoronary injection of 0.5 to 4 mg, e.g., about 1.0 mg, of propranolol is administered by intracoronary infusion through a drug delivery catheter positioned in the right coronary artery just proximate to the AV node artery, over a time period of about 0.5–3 minutes, e.g., about 1 minute, preferably followed by a saline flush, such as a 2 mL saline flush. This is followed by an intracoronary bolus injection of about 0.01 to 0.5 mg, e.g., about 0.025 to 0.3 mg, e.g., about 0.1 mg carbachol administered over about 0.5 to 3 minutes, e.g., about 1 minute, and then by an intracoronary infusion of carbachol at a rate of about 0.01 to 0.3 mg/min, e.g., about 0.025 to 0.3 mg/min, for example, about 0.01 to 0.1 mg/min, or, e.g., about 0.05 to 0.1 mg/min, e.g. about 0.0825 mg/min, for a time period of about 5 to 90 minutes, preferably about 30 to 90 minutes, e.g., about 75 minutes. A dosage amount of phenylephrine in the range of about 0.1 to 1.0 mg if needed may be administered to counteract any hypotension effects associated with carbachol administration. Additionally, nitroglycerine may be required in some patients to counteract the coronary vasodilator effects of systemic phenylephrine administration.

Additionally, in one embodiment, where the patient is under prior therapeutic treatment with a β-blocker, lower amounts of β-blocker, or alternatively no β-blocker may be required prior to the surgical procedure. Moreover, in certain situations overdrive suppression (i.e., pacing at about 90 to 110 beats/min for about 10 seconds) may be used in addition to the initial intracoronary bolus of carbachol and propranolol to initiate ventricular asystole prior to carbachol continuous infusion.

Compositions may be administered by intravenous, intracoronary and intraventricular administration in a suitable carrier. Compositions may be administered locally to the heart, for example, by direct infusion to the right coronary artery as a single bolus injection, continuous infusion, or combination thereof. This can be achieved, for example by administration to the proximal or ostial portion of the right coronary artery, using a guiding catheter or drug delivery catheter, or by administration just proximal to the AV node artery by means of a drug delivery catheter positioned in the right coronary artery. Intraventricular (left side) injection also may be used. Continuous infusion can be continued as long as necessary to complete the procedure. In one embodiment, the infusion rate can range from about 0.01 to 0.5 mg·min$^{-1}$, e.g., about 0.01 to 0.3 mg·min$^{-1}$, or about 0.015 to 0.15 mg·min$^{-1}$, for example about 0.016 to 0.12 mg·min$^{-1}$. Methods of administration include intravenous, intra-atrial, intra-aortic, and administration via the aortic root, or coronary artery. Administration may be via any suitable route, for example via the left or right ventricle, for example proximal to the AV node artery, or via the aorta, pulmonary artery, pulmonary vein, middle cardiac vein, right atrium or the coronary sinus. In another embodiment, administration may be by direct administration into the AV node artery or AV node. In one embodiment, administration may be via a hypodermic needle to the AV node.

In addition to local delivery, systemic delivery routes of administration known in the art may be used, such as oral, transdermal, intranasal, suppository and inhalation. For example, in addition to injection as described above, the β-blocker may be administered orally in a suitable carrier for oral administration. The patient also may be on therapeutic treatment with a β-blocker prior to the surgical procedure and thus may require lower amounts, or even no additional β-blocker prior to the surgery.

The compositions capable of inducing ventricular asystole, such as an AV node blocker and β-blocker, may be provided in pharmaceutically acceptable carriers including diluents. A variety of carriers may be used that are known in the art, preferably in sterile form. Suitable carriers include sterile water, aqueous normal saline solutions, and aqueous solutions such as lactated Ringer's solution, or a solution of a sugar such as dextrose, for example 5% dextrose in water or saline. Other possible carriers, which may be provided, for example, in an aqueous solution, include sodium citrate, citric acid, amino acids, lactate, mannitol, maltose, glycerol, sucrose, ammonium chloride, NaCl, KCl, CaCl$_2$, sodium lactate, and sodium bicarbonate. In one embodiment, the carrier may be D5W, a solution of 5% dextrose in water. Other carriers include buffered aqueous solutions, such as an acqueous solution comprising 5 mM HEPES (N-[2-hydroxyethyl)piperazine-N'-[2-ethanesulfonic acid]). Antioxidants or preservatives such as ascorbic acid also may be provided in the compositions. Carriers known in the art, for example, for injection, oral delivery, delivery via a suppository, transdermal delivery and inhalation also may be used.

In one embodiment, compositions are provided which include an AV node blocker, such as a cholinergic agent and β-blocker either together or separately in a pharmaceutically acceptable carrier. In another embodiment, containers containing unit dosage forms of the AV node blocker, such as a cholinergic agent and the β-blocker, either in separate containers or in a single container are provided. In one embodiment, unit dosage forms of carbachol and propranolol are provided either in separate containers or in a single container for administration to a patient, optionally in combination with a pharmaceutically acceptable carrier. For example, carbachol can be present in a pharmaceutically acceptable carrier in a dosage form for administration to a patient in an amount of about 5 to 150 μg/kg body weight of the patient, or in a total amount of from about 1 to 20 mg, or in a total amount of about 5 to 10 mg. The propranolol can be present in a pharmaceutically acceptable carrier in a dosage form for administration to a patient in an amount of about 0.01 to 0.07 mg/kg body weight of the patient, or in a total amount of about 1 to 10 mg, or in a total amount of about 1 to 5 mg. Carbachol is available commercially from Sigma Chemical Company, St. Louis, Mo.

Thus, in one aspect of the invention, there is provided a composition comprising an AV node blocker or a β-blocker, or a combination thereof, in a pharmaceutically acceptable carrier. The composition, may be provided for example as an aqueous solution, or in the form of a suspension or emulsion. Optionally, the composition may include a mixture of AV node blockers and/or a mixture of β-blockers. The composition may be provided in a form suitable for parenteral administration. In the embodiment wherein the composition comprises water, the water is preferably processed, for example by compression distillation, to ensure that it is sufficiently purified to be suitable for parenteral administration. Methods for making compositions of a quality suitable for parenteral administration are disclosed for example, in Gennaro, "Remington: The Science and Practice of Pharmacy," Mack Publishing Co., Easton, Pa. 1995, Vol. 2, Chapter 87, the disclosure of which is incorporated herein. In one embodiment, the composition is provided in a form suitable for administration to the cardiovascular system during a surgical procedure. In one embodiment, the AV node blocker is a cholinergic agent. In a preferred embodiment, the AV node blocker is carbachol. The pharmaceutically acceptable composition comprising the AV node blocker or β-blocker, or combination thereof, may be provided, for example in an aqueous solution, in a container, such as a vial, at a concentration suitable for direct administration to a patient, or may be diluted, for example with saline.

In one embodiment, a pharmaceutically acceptable composition comprising an AV node blocker, such as cholinergic agent, is provided, which may be used to permit local cardiac administration of the AV node blocker. In one embodiment, there is provided a pharmaceutically acceptable composition comprising carbachol, wherein the composition is suitable for parenteral administration. Preferably, the carrier is suitable for intracoronary administration. The carbachol may be provided in an aqueous carrier, such as water. In the composition, which optionally may be diluted prior to local cardiac administration, the concentration of carbachol may range, for example, from about 0.01 mg/mL to 2.55 mg/mL, e.g., about 0.1 to 1.0 mg/mL. In one embodiment, the composition may further comprise a β-blocker, such as propranolol, at a concentration, for example, of about 0.5 to 6 mg/mL, for example about, 0.5 to 3 mg/mL, or, e.g., about 1.0 to 2.0 mg/mL or about 1.0 mg/mL. If needed, the composition may be diluted to a concentration suitable for local administration to the heart, e.g., via an intracoronary bolus or infusion.

Pharmaceutically acceptable compositions also are provided including an AV node blocker, such as a cholinergic agent and/or a β-blocker that are suitable for direct local cardiac administration. In one embodiment, there is provided a pharmaceutically acceptable composition comprising carbachol, wherein the composition is suitable for direct local administration, for example, to a coronary vessel such as the right coronary artery. The carbachol is, for example, provided in an aqueous carrier, such as water. In one embodiment, the carbachol is provided in physiologic saline. In the composition, the concentration of carbachol may range, for example, from about 0.001 to 2.55 mg/mL, for example, about 0.01 to 2.5 mg/mL, or about 0.05 to 1.0 mg/mL, e.g., about 0.01 to 0.5 mg/mL, for example, about 0.05 mg/mL to 0.2 mg/mL, or e.g., about 0.1 to 0.2 mg/mL, or about 0.075 mg/mL. The composition may optionally further comprise a β-blocker, such as propranolol, at a concentration, for example, of about 0.05 to 6.0 mg/ml, for example, 0.05 to 3.0 mg/ml, or, e.g., about 1.0 to 2.0 mg/ml, or about 1.0 mg/ML. In this embodiment, the composition is suitable without dilution for local administration to the heart, e.g., via an intracoronary bolus or infusion.

In another aspect of the invention, there is provided a surgical kit including a container comprising a dosage of a cholinergic agent, such as carbachol. In one embodiment, a surgical kit is provided that includes a first container comprising a cholinergic agent and a second container comprising a β-blocker, wherein in one preferred embodiment, the cholinergic agent is carbachol and the β-blocker is propranolol. The containers may include respectively a preferred dosage form of the carbachol and of the propranolol. The first container may include a carbachol in a pharmaceutically acceptable carrier, and the second container may include propranolol in a pharmaceutically acceptable carrier. Alternatively, the cholinergic agent and the β-blocker may be provided in a single container, optionally in combination with a pharmaceutically acceptable carrier. The kit may further include epicardial or endocardial pacing electrodes or any other disposable items associated with the pacemaker. The kit also may include a drug delivery catheter and associated disposable items.

Referring to the drawings where like numerals indicate like elements, drug delivery and pacing apparatus are shown in accordance with the principles of the present invention. The pacing system generally includes pacer, a switch box and an actuator, which preferably can be readily controlled by the physician to remotely control the pacer through the switch box. The pacing system will be described with reference to the example illustrated in FIG. 1. However, it should be understood that other configurations may be used.

Referring to FIG. 1, a pacing system configured in accordance with the present invention is shown. The illustrative system generally includes a pacer 18, a switch or control box 14, and an actuator, such as actuator 22 or 24. Pacer 18 may be a conventional ventricular demand pacer or dual chamber (atrial-ventricular) pacer. Leads 16 couple the output of pacer 18 to switch box 14 and leads 12 couple switch box 14 to the patent's heart. The latter may be achieved for example, either endocardially or epicardially. Switch or control box 14 preferably is configured so that when actuated, it delivers the pacing signals or output of pacer 18 to leads 12. Conductor or lead 20 couples remote actuator 22 to switch box 14. Although a conventional foot pedal type actuator is shown, it should be apparent from the foregoing and following discussion that other actuators such as handle held actuator 24 (shown in phantom) may be used. Further, as an alternative to epicardially or endocardially placed pacing leads, the leads may be transvenously delivered for coupling to the heart. In a further alternative, electrodes, such as transarterial electrodes, can be incorporated into the drug delivery catheter.

This pacing system of the present invention preferably provides to the surgeon remote control of the on/off pacing function only. All other parameters which are user selectable (rate, output, etc.) preferably are not remotely programmable but must be adjusted by using controls on the pacemaker.

Figure 1A:
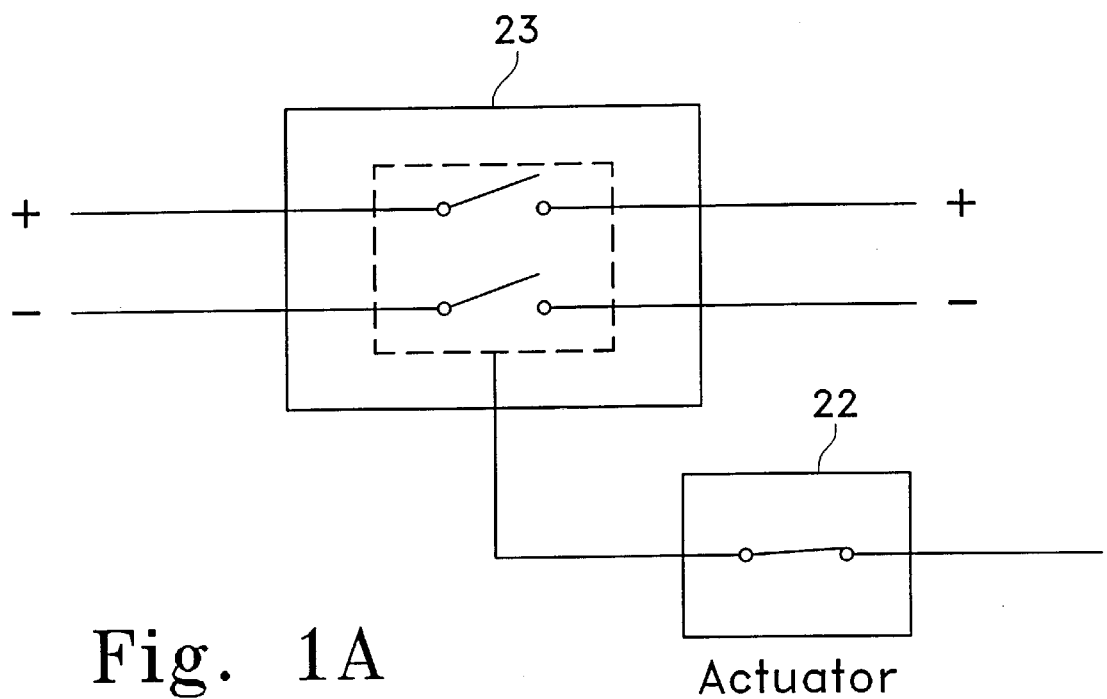
FIGS. 1A and 1B are circuit diagrams of a control switch and an actuator used in the pacing system of FIG. 1.
Figure 1B:
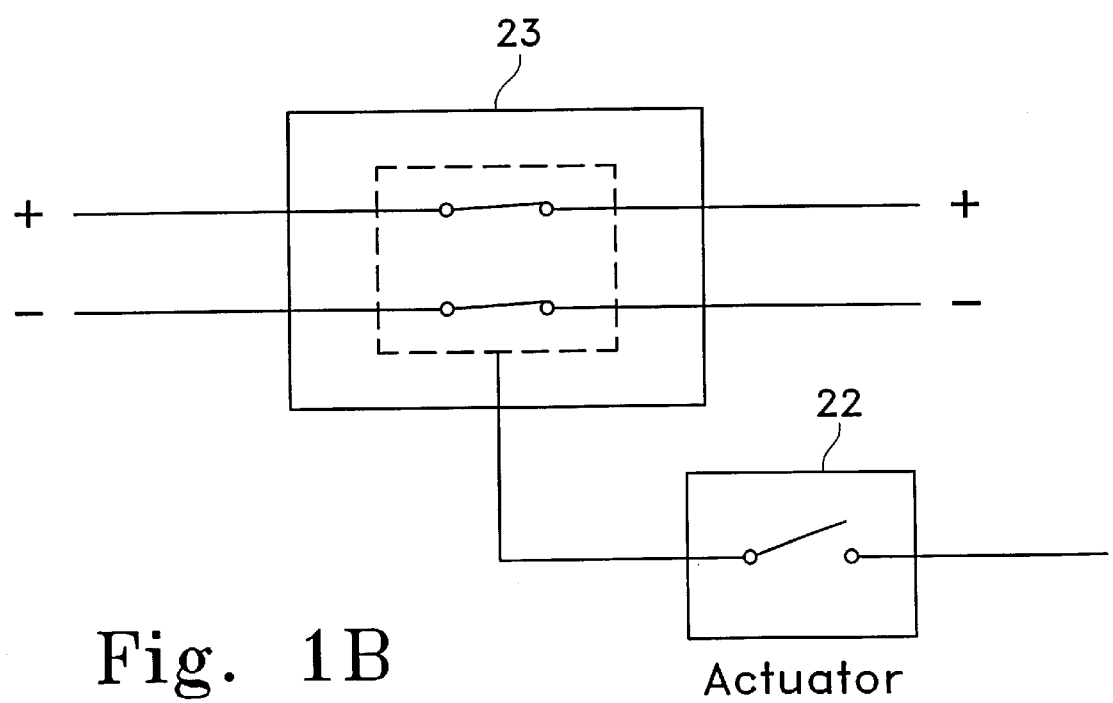

Referring to FIGS. 1A and 1B, circuit diagrams of the pacing system of FIG. 1 are shown. Switch box 14 includes an electrical or mechanical switch 23 to which actuator 22 couples. This coupling allows the switch to be energized or deenergized as would be apparent to one of ordinary skill. Preferably, foot pedal 22 is configured to be in an "Off" (electrically open) position when in its normal state and to be in an "On" (electrically closed) position to open switch 23 in switch box 14 and interrupt delivery of pacing signals to the heart when the pedal is depressed. Accordingly, if the power source to the pedal is interrupted, the heart will be paced. Alternatively, the foot pedal may be configured to be in an "On" position when in its normal state and to be in an "Off" position when the pedal is depressed.

Returning to FIGS. 1A and 1B, switch box 14 preferably is configured in a manner to allow the pacing signal to pass through the box, to leads 12 and, thus, to the patient while actuator 22 is in the "Off" position. As shown in FIG. 1A, the switch box's switch 23 opens when the actuator is activated (e.g., the foot pedal is depressed). This opening prevents the pacing signal from going to the patient. On the other hand, as shown in FIG. 1B, the switch box's switch 23 closes to again allow the pacing signal to pass through to the patient, when the actuator is released. Commercially available switch boxes and foot pedal actuators may be used. For example, a suitable switch box with foot pedal is the Treadlight 2, Catalogue No. T-91-S manufactured by Line Master Switch Corporation. This switch provides an open circuit when actuated as shown in FIG. 1A.

Safety features may be incorporated into the switch box. The first is a timer or override circuit, either programmable or factory set, that limits the time the switch or control box can interrupt the pacer. This circuit overrides the actuator, if the actuator should happen to be held down (i.e. in the "On" position) too long, i.e., longer than the preset maximum time. The override circuit may be set or configured to override the activator after an interval of time of about 0.1–60 seconds, more preferably about 5–30 seconds, or more preferably about 10–15 seconds.

A second safety feature is an indicator (visual and/or audible) that indicates the pacing signal is not being sent to the patient. A third safety feature is an indicator (visual or audible) that the pacing signal is going out from the control box to the patient, especially to signify the end of an interruption period (resumption of pacing). Preferably, the indicator or indicators are audible signals.

The control box could have additional features that may be more useful for the user than for safety. The first feature would be an indicator, preferably audible, preparing the user for the resumption of pacing. This could be a beeping tone that increases in frequency as the interruption period ends. Second, the control panel should be battery powered either by a disposable or rechargeable battery. Other features include a control box that is preferably within 7"×10"×5", lightweight, less than 3 pounds, and easy to use with current pacer and pacing lead designs.

Figure 1C:
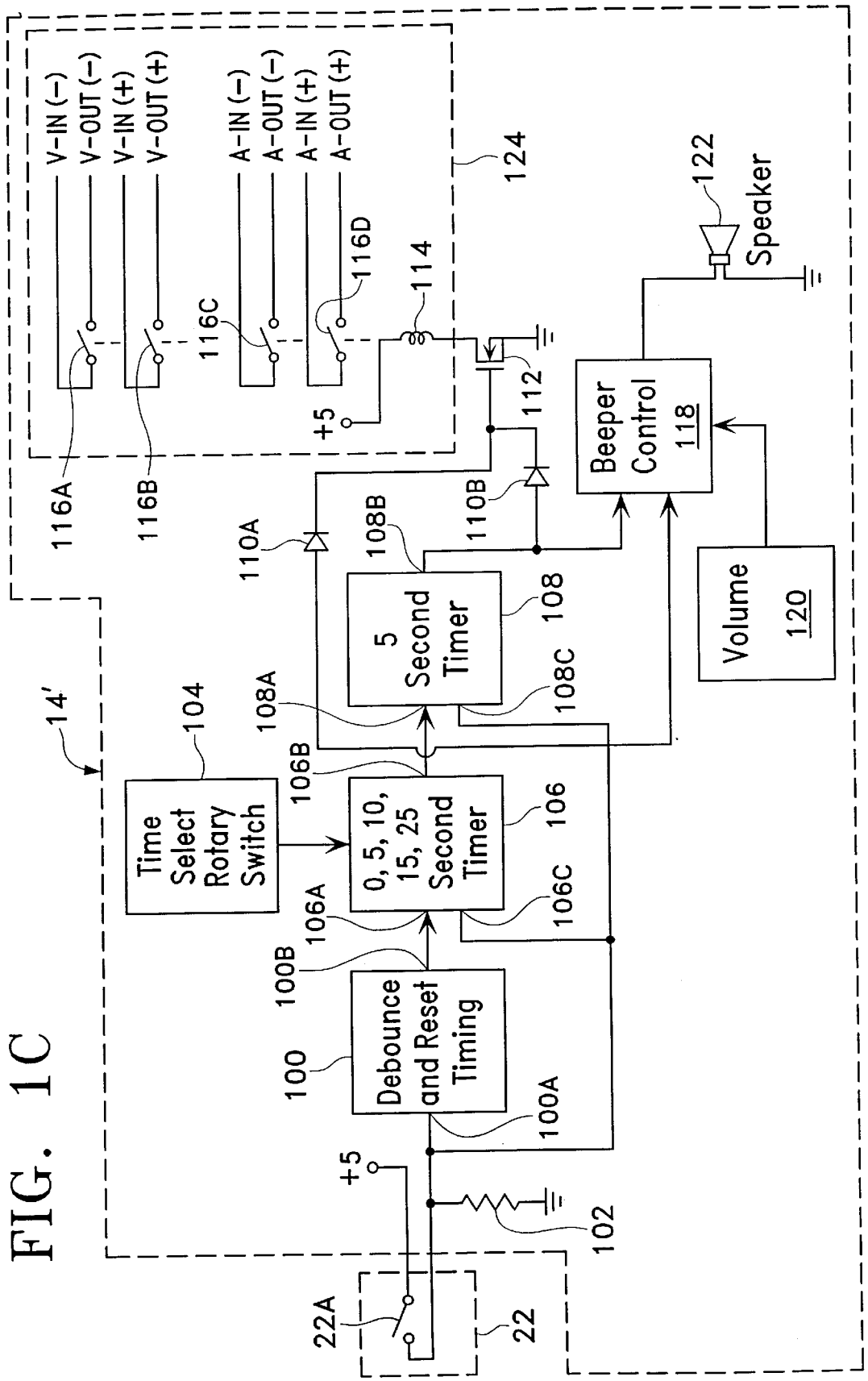
FIG. 1C is a schematic representation of a control box according to the present invention.

FIG. 1C presents one embodiment of the control box as schematically shown in FIGS. 1, 1A and 1B. As shown in FIG. 1C, a suitable control box 14' includes debounce circuit 100, pull-down resistor 102, timer select switch 104, first timer 106, second timer 108, diodes 110, transistor 112, inductive solenoid coil 114, switches 116, beeper control 118, volume control 120, and speaker 122.

Control box 14' uses debounce circuit 100 to generate a steady signal when mechanical foot pedal 22 is depressed. Debounce circuit 100 has an input terminal 100A and an output terminal 100B. The input terminal connects to pull-down resistor 102. This terminal also connects to the foot pedal switch 22A of foot pedal 22. When the foot pedal switch is open as shown in FIG. 1C (e.g., when the operator does not depress the foot pedal), the input terminal is pulled to ground through pull-down resistor 102. On the other hand, when the foot pedal switch closes (e.g., when the operator depresses the foot pedal), the input terminal connects to the power supply voltage source through the foot pedal switch 22 in order to receive the power supply voltage. In response to the power supply voltage provided by mechanical foot pedal 22, the debounce circuit generates a signal on its output terminal that it steadily maintains at one level (e.g., the ground level) until the foot pedal switch opens.

As shown in FIG. 1C, the output terminal 100B of the debounce circuit 100 connects to first timer 106. The voltage on this output terminal is usually in a first level (e.g., the power supply voltage) when the input to the debounce circuit is pulled to ground (i.e., when the foot pedal has not been depressed). However, this output terminal's voltage transitions to a second level (e.g., the ground voltage) when the input to the debounce circuit transitions to the power supply voltage (i.e., when the foot pedal has been depressed). As further described below, the voltage at the output terminal 100B in combination with the signal supplied to the reset pin 106C of the first timer circuit controls the operation of this timer circuit.

Control box 14' uses first and second timer circuits 106 and 108 in order to measure the lapse of a selected period of time. The amount of time selected on time select rotary switch 104 is the maximum amount of time that the physician can interrupt the supply of the pacing signal to the heart by depressing the foot pedal. Once the control box 14' determines, through the use of timers 106 and 108, that the maximum amount of time has expired, then the control box 14' overrides (ie., ignores) the signal generated by the depressed foot pedal and resumes the supply of the pacing signal to the patient. The second timer counts the last five seconds in the selected period of time, while the first timer counts the remainder of time.

Both the timers 106 and 108 have reset pins (ie., reset terminals) 106A and 108A that receive the signal supplied to input terminal 100A of debounce circuit 100. When the signal supplied to the reset pin of a timer is low (i.e., when the foot pedal has not been depressed), the timer enters its reset mode and resets its measured time value to its initial value. Each timer exits its reset mode and enters a standby mode when the signal supplied to its reset terminal is high (i.e., when the foot pedal has been depressed).

Also, each timer enters its operational modes when it receives a trigger signal at its input after it has entered its standby mode. Once the timers are in their operational modes, they start counting up or down to their expiration values when they receive an appropriate signal (e.g., a high voltage) on their input terminals 106A, 108A. First timer 106 receives its trigger signal from the output of the debounce circuit. Thus, the transition of the output of the debounce circuit from one state to another (e.g., goes from a high level to a low level) triggers the operation of the first timer 106. Once triggered, the first timer 106 starts to count towards its expiration value. The physician determines the expiration value of the first timer by operating the timer select switch 104, which connects to the first timer.

While the first timer operates (i.e., while it counts) and before it has reached its expiration value, the signal at this timer's output terminal 106B is at a first voltage level (e.g., the power supply level). The signal from output terminal 106B flows through diode 110A and is supplied to the gate of transistor 112 to turn ON this transistor. Transistor 112 can be any type of transstor. In FIG. 1C, this transistor is an NMOS device.

Once transistor 112 turns ON, it draws current from the power supply through the inductive solenoid coil 114. This coil serves as a relay (i.e., coil that when energized operates a mechanical switch). Thus, when current passes through the solenoid coil, it activates the relay which opens switches 116A–D of patient connect relay 124. When the relay is deactivated, switches A–D couple the signal from the pacer to the patient through leads 12.

Figure 1D:
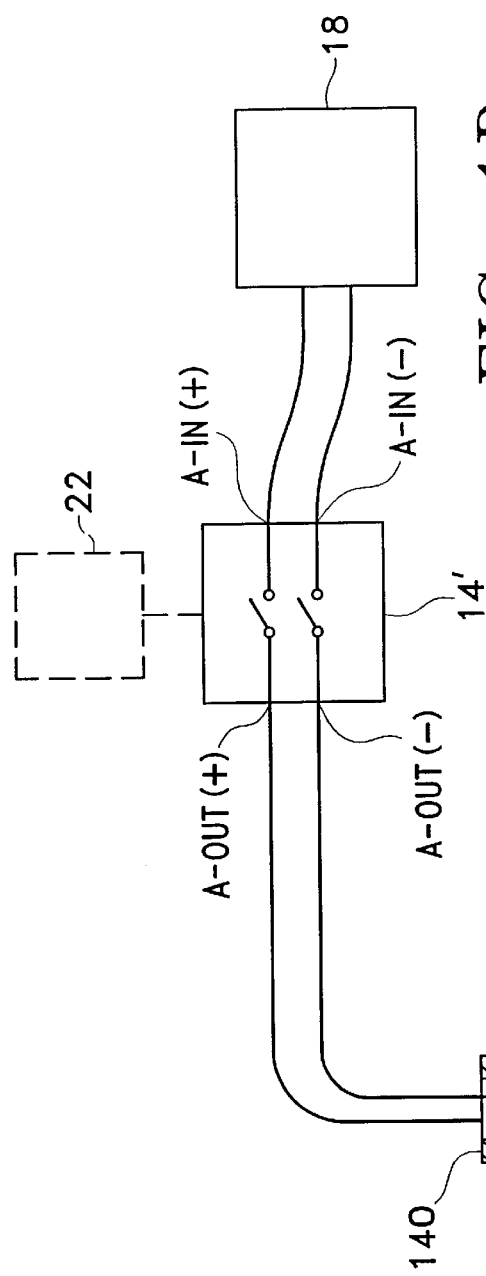
FIG. 1D diagrammatically shows one outlet lead arrangement coupled to the heart of a patient.
Figure 1E:
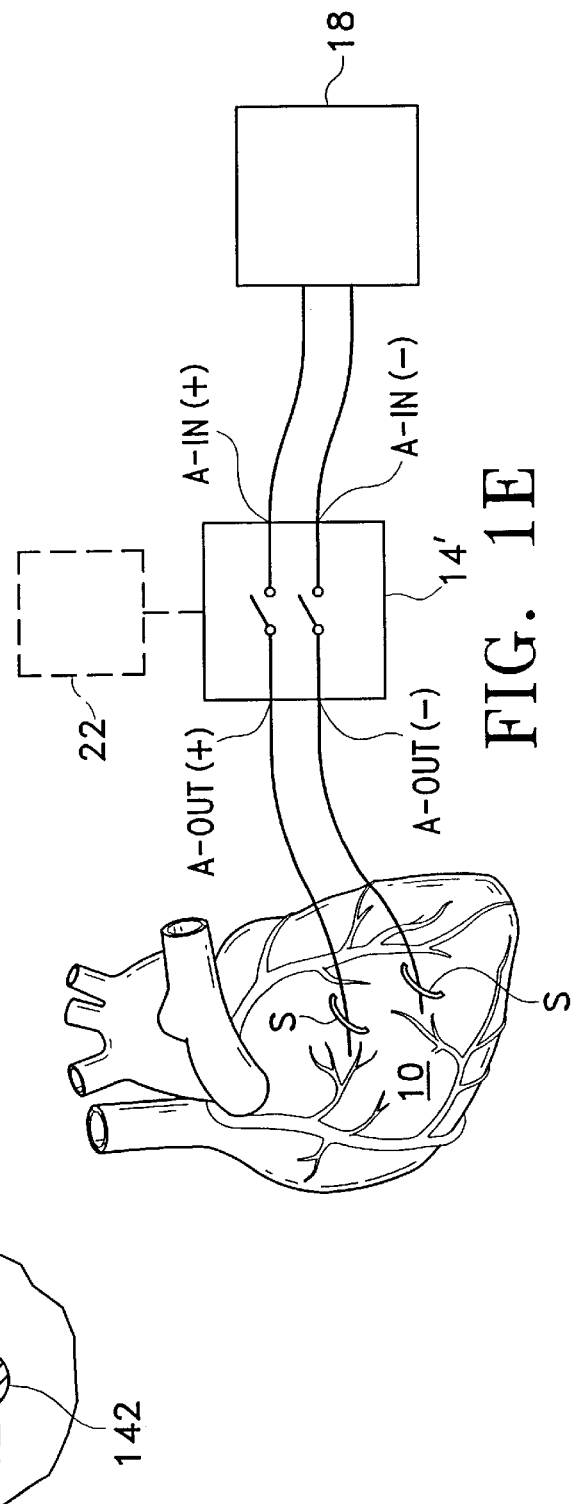
FIG. 1E diagrammatically shows another outlet lead arrangement coupled to the heart of a patient.

Referring to the embodiment illustrated in FIG. 1C, switch 116A couples a ventricle inlet (V-IN(−)) to a ventricle outlet (V-OUT(−)). Switch 116B couples a ventricle inlet (V-IN(+)) to a ventricle outlet (V-OUT(−)). Switch 116C couples an atrial inlet (A-IN(−)) to an atrial outlet (A-OUT (−)), while switch 116D couples an atrial inlet (A-IN(+)) to an atrial outlet (A-OUT(+)). The inlets are coupled to the pacer and the outlets are coupled to the patient. Referring to FIG. 1D, a schematic representation of an endocardial lead arrangement between the control box and the right atrium of a patient is shown, together with the coupling between the control box and the pacer. An actuator may be coupled to the control box as described above. The inlets (A-IN(−), A-IN (+)) may be coupled to the pacer 18 adapter cables and the outlets (A-OUT(−), A-OUT(+)) may be coupled to the patient with leads as shown in the drawing and as would be apparent to one of ordinary skill. Specifically, one lead may be coupled to positive terminal 140, which is in the form of a ring, and the other lead may be coupled to a negative terminal 142, which may have a generally hemispherical configuration. A similar arrangement can be used to couple the control box to the right ventricle. Although an endocardial lead configuration is shown in FIG. 1D, epicardial leads as shown in FIG. 1E may be preferred. Specifically, epicardial leads, which may be sutured to the heart (e.g., right atrium) as shown in FIG. 1E and generally designated with reference character "S", generally are preferred in open chest procedures since they can be readily sutured to the heart. Again, a similar arrangement can be used to couple the control box to the right ventricle.

Although the patient connect relay 124 is shown as a dual chamber pacing system, it should be understood that single chamber pacing systems can be used to pace the ventricle as would be apparent to one of ordinary skill in the art (e.g., by only using switches 16A and B shown in FIG. 1C).

The output of the first timer is also supplied to a beeper control circuit 118, which controls the output of a speaker 122. Hence, when the first timer's output is active (i.e., its at a first voltage level, such as the power supply level), it turns ON the beeper control circuit, which in turn generates a first audible signal through speaker 122.

When the first timer expires (i.e., when it has reached its expiration value), the signal at its output terminal transitions from the first voltage level to a second voltage level (e.g., transitions from the power supply level to ground level). The first timer then enters its standby mode, where it will stay until it is reset by the opening of the foot pedal switch.

The second timer has an edge detector (e.g., a negative edge detector) that detects this transition. Once it detects this transition, the second timer transitions into its operation mode, and thereby starts to count towards its expiration value. The second timer's expiration value is set at five seconds.

While the second timer is in its operation mode and has not reached its expiration value, the signal at its output terminal is at a first voltage level (e.g., the power supply level). In turn, diode 110B supplies this signal to the gate of transistor 112, and thereby keeps this transistor ON. While transistor 112 is ON, it continues to draw current through the coil 114, which, in turn, keeps switches 116A–D, which control delivery of the pacer signal to the patient, open.

The output of the second timer is also supplied to a beeper control unit. Hence, when this output is active (i.e., its at a first voltage level, such as the power supply level), it turns ON the beeper control unit, which in turn generates a second audible signal through speaker 122.

Finally, it should be noted that the output of the timers resets to the second voltage level (e.g., ground) whenever the foot pedal switch opens and the timers are reset. This resetting operation overrides the counting operation of the timers. Thus, if the timers are in the process of counting, the opening of the foot pedal makes these timers stop counting and reset. Any suitable timers may be used such as 555 timers manufactured by National Semiconductor (Santa Clara, Calif.).

As an alternative to foot pedal 22, a conventional needle holder 24 can be used to control the pacer switch box. In this case, the needle holder preferably is of the standard Castro-Viejo variety. However, any other manual switch actuator operable by the surgeon for opening and closing the switch in switch box 14 on demand can be used in accordance with the invention to electrically connect and disconnect pacer 18 with pacing leads 12. Thus, the actuator can be incorporated in or on one of the surgeon's instruments, such as surgical site retractor, or any other location easily and quickly accessed by the surgeon.

Any conventional pacer suitable for ventricular demand pacing and having external leads that can be electrically coupled to a switch box 14 may be used. An example of such a suitable pacer is the Medtronic model 5330 or 5375, Demand Pulse Generator manufactured by Medtronic Inc. (Mpls, Minn.)

It should be understood that although a particular pacing configuration is shown, other configurations may be used. For example, the pacer and switch box may be combined in a single unit. If the switch box is incorporated in a pacer (i.e., pacemaker), specifications of the pacemaker should be similar to currently manufactured external pacemakers (e.g., Ventricular or atrial-ventricular sequential; Rate range: 30 to 180 ppm (pulses per minute), continuously adjustable or in increments of 1 ppm; Output current range: 0.1 to 20 mA; Sensitivity range: 1.0 mV(maximum) to asynchronous; Pulse width: 1.8 ms maximum).

Pacer 18 preferably is an extracorporeal pacer and differs from implantable pacemakers in the following ways. Pacer 18 typically will be in excess of 400 grams, can use replaceable (battery life of approximately 500 hours) or rechargeable batteries (9v), may be line power designed to last several years, and need not be constructed with a biocompatible exterior shell or be hermetically sealed.

Further, the pacing system may be configured to synchronize activation and deactivation of the patient's ventilator (not shown) with pacing. For example, the control box may be configured for coupling to a ventilator so that pacing and ventilator signals are simultaneously delivered to the patient leads 12 and the ventilator when the actuator is in a first state (e.g., when the foot pedal is released). In this example, the pacing and ventilator signals are simultaneously interrupted when the actuator is in a second state (e.g., when the foot pedal is depressed). The synchronization of pacing with a ventilator may minimize or eliminate unwanted heart motion associated with a patient's breathing with a ventilator.

Figures 2, 2A:
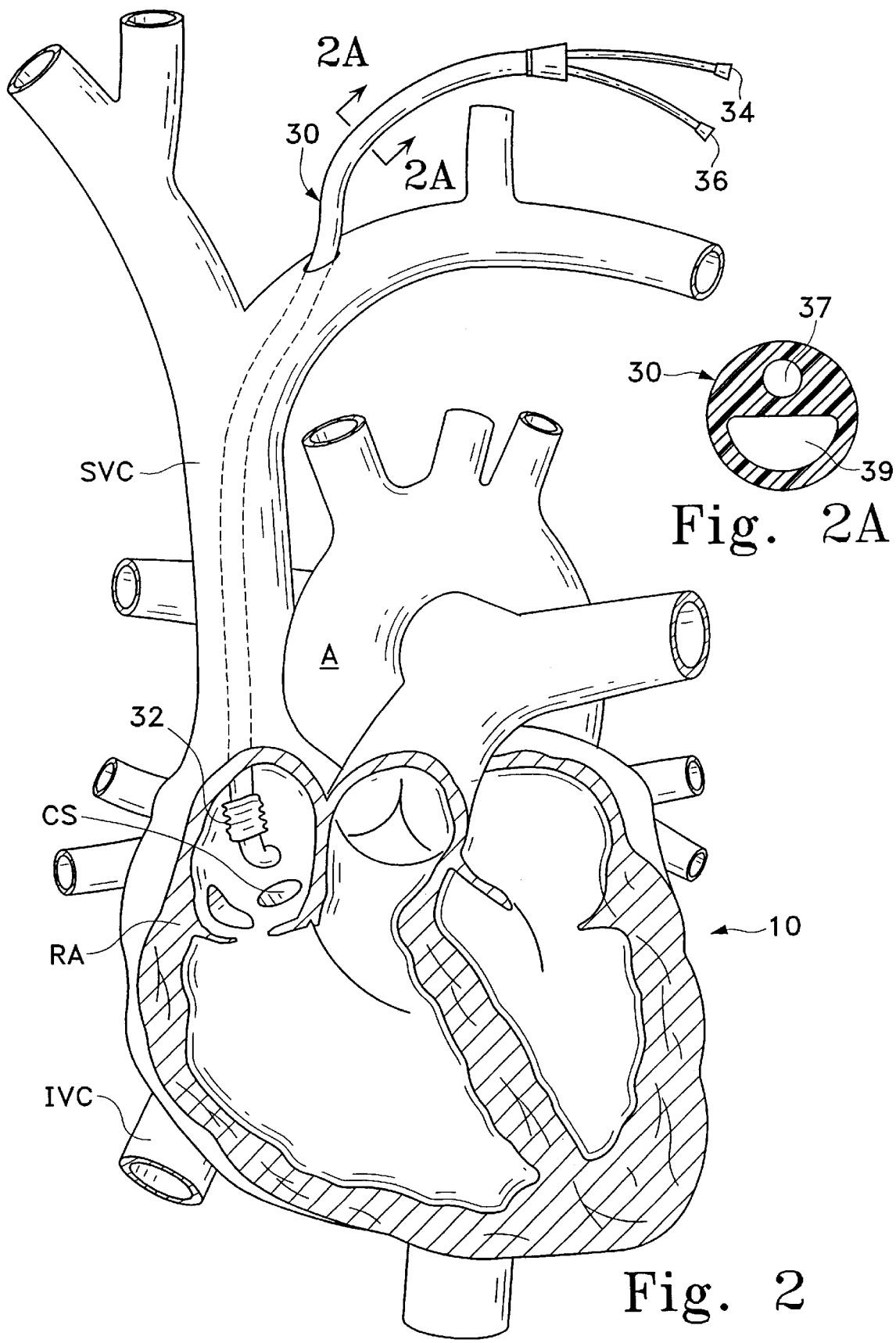
FIG. 2 illustrates a drug delivery catheter prior to insertion into the coronary sinus in accordance with the invention.
FIG. 2A is a sectional view of the catheter of FIG. 2 taken along line 2A—2A.
Figure 3:
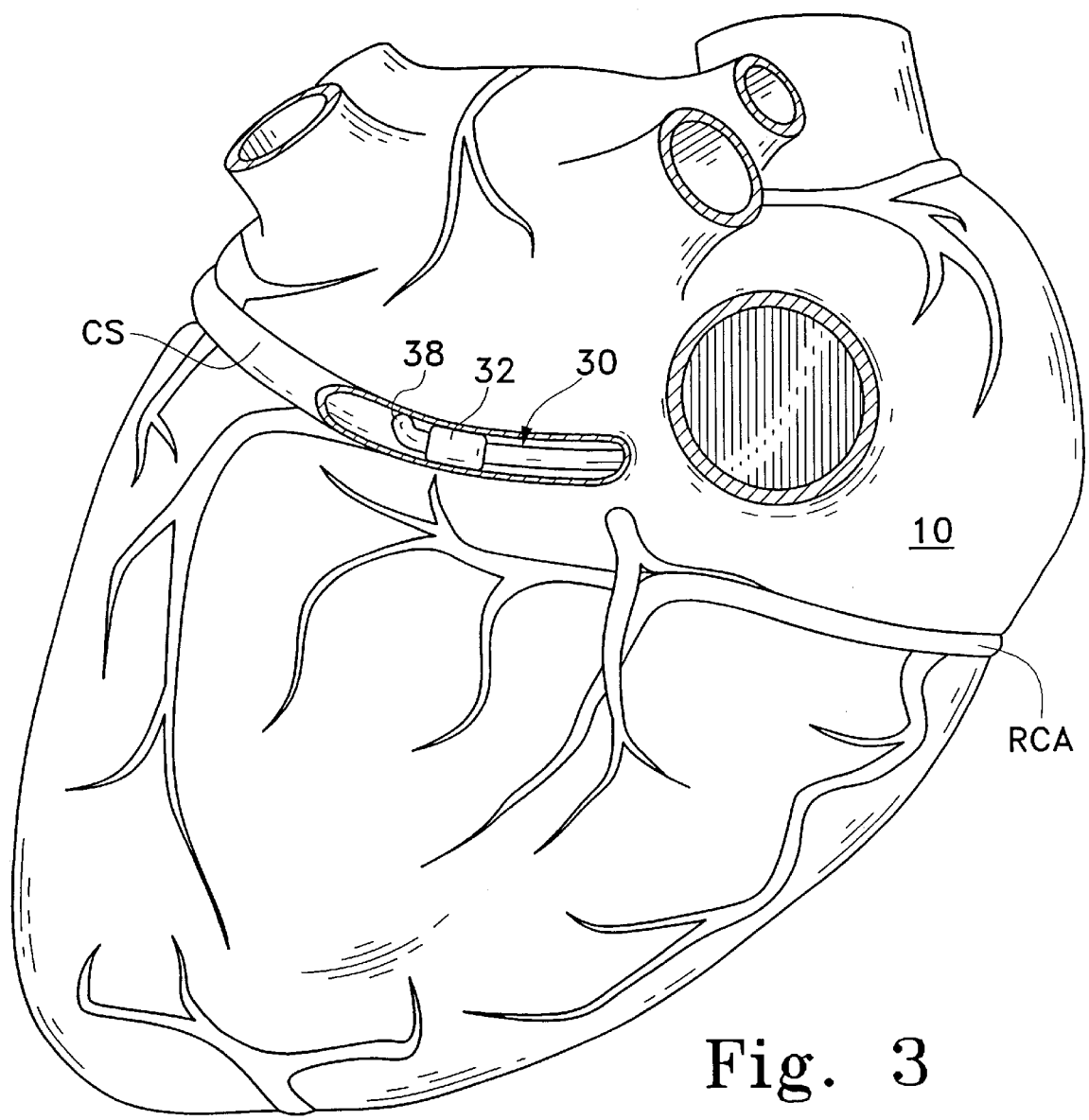
FIG. 3 illustrates placement of the distal end portion of the catheter of FIG. 2 in the coronary sinus.
Figure 3A:
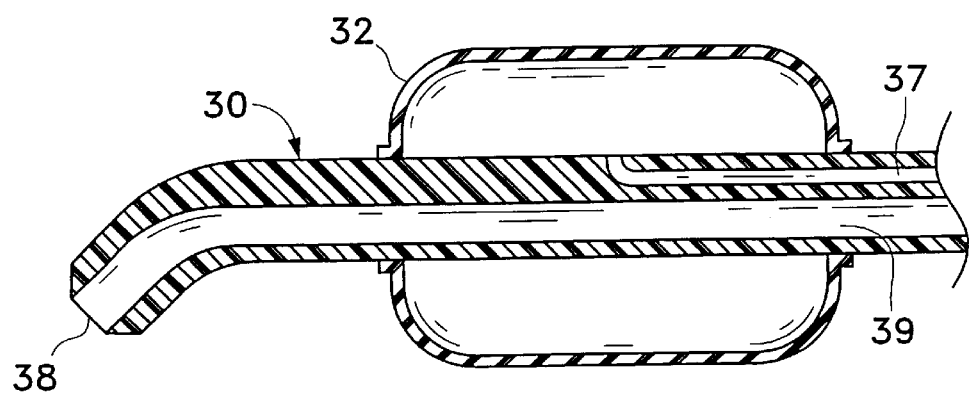
FIG. 3A is a sectional view of the distal portion of the catheter of FIG. 3.
Figure 4:
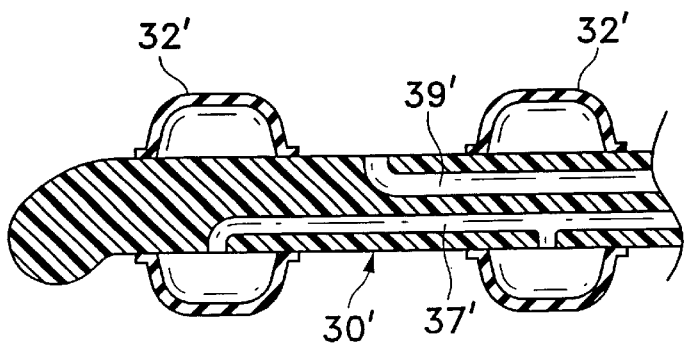
FIG. 4 illustrates another coronary sinus catheter configuration.
Figure 5:
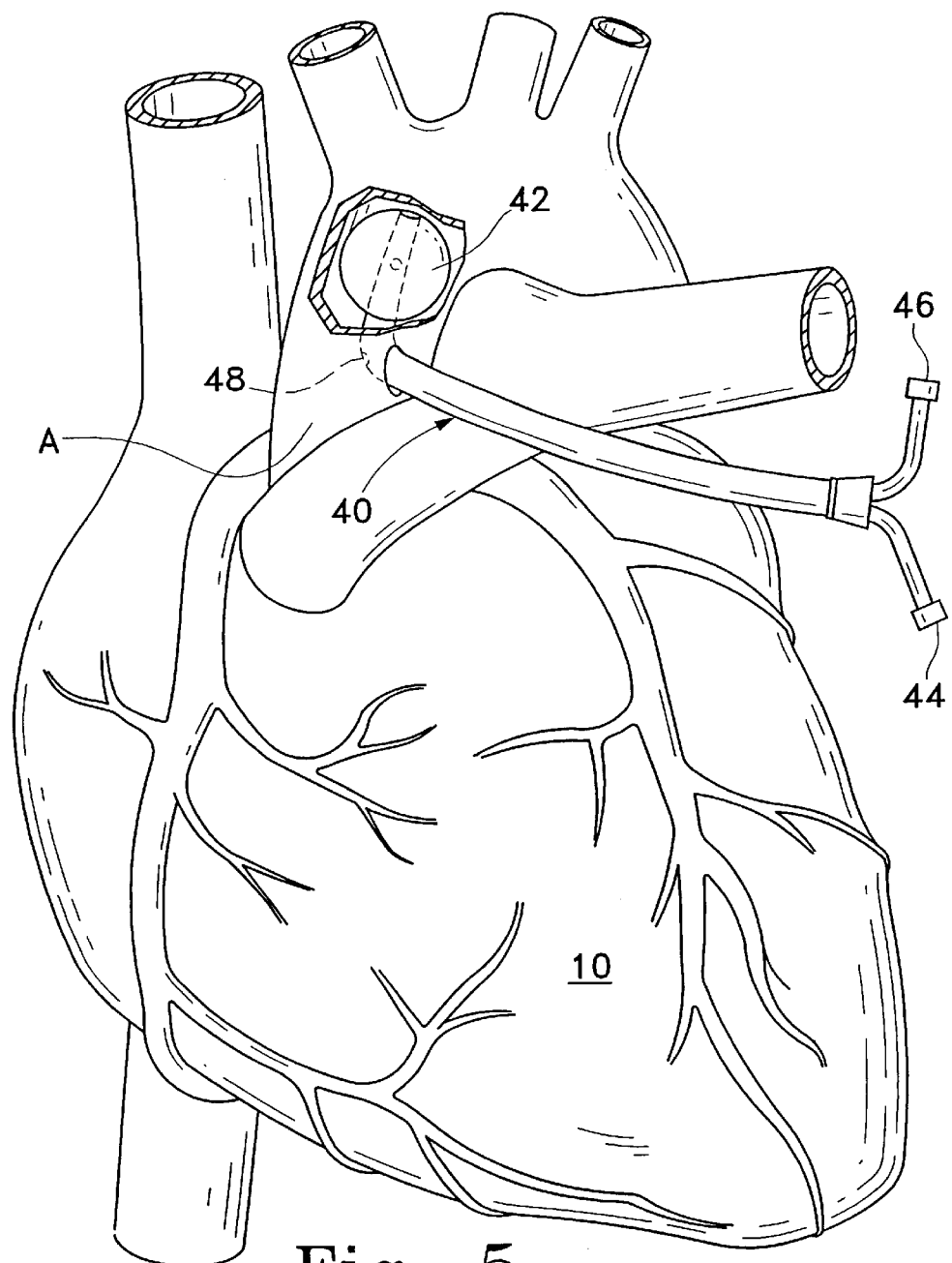
FIG. 5 depicts a drug delivery catheter positioned for intra-aortic drug delivery in accordance with the present invention.
Figure 6:
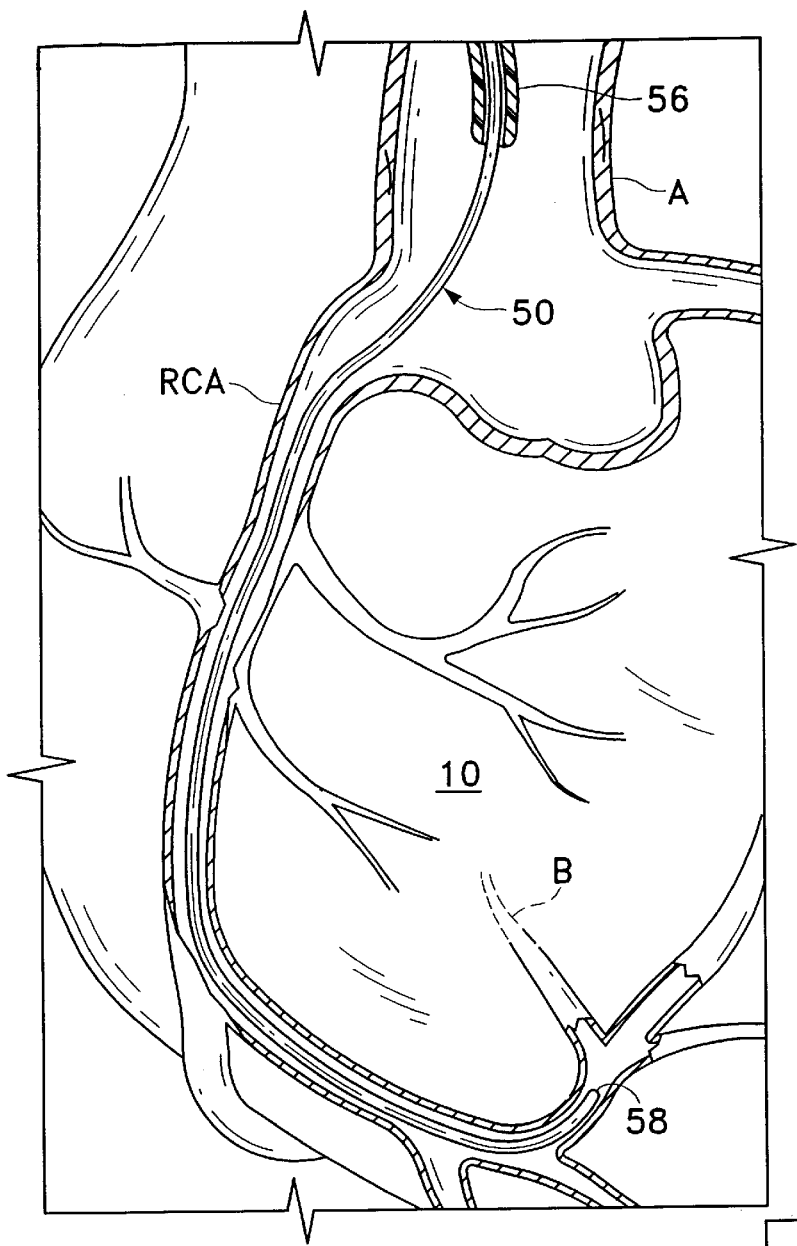
FIG. 6 illustrates a drug delivery catheter positioned for drug delivery local to the AV node branch in accordance with the present invention.
Figure 7:
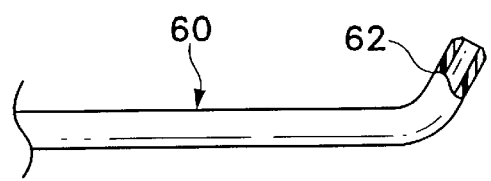
FIG. 7 illustrates another embodiment of the catheter of FIG. 6 showing a curved distal end portion for directing fluid toward the AV node.

With an understanding of the pacing system in hand, drug delivery according to the principles of the invention will be described with reference to FIGS. 2–7. Generally, FIGS. 2 and 3 show delivery into the coronary sinus (FIG. 4 shows an alternative balloon configuration); FIG. 5 shows intra-aortic delivery; and FIGS. 6 and 7 show delivery through the right coronary artery. Discussion of a further delivery procedure in accordance with the present invention, intraventricular injection, also will be provided.

Coronary Sinus Injection

Referring to FIGS. 2, 2A, 3, and 3A, a coronary sinus delivery catheter 30 is shown for local drug administration into the coronary sinus (CS) according to the present invention. Coronary sinus delivery catheter 30 preferably is a medium-diameter, e.g. about 6–8 French, single or dual lumen, flexible catheter. The tip of catheter 30 may be curved slightly to give a so-called hockey-stick appearance as shown in the drawings. This configuration facilitates, for example, introducing the catheter into the coronary sinus from the atrium as shown in FIG. 2 where the distal tip is shown prior to introduction into the coronary sinus. A low-pressure balloon 32 of up to about 2 cm in diameter is located near the tip of the catheter. Two ports 34, 36 are present at the proximal portion of catheter 30 for balloon inflation and drug injection, respectively. Catheter 30 further includes inflation lumen 37 and drug delivery lumen 39 (FIGS. 2A and 3A) which fluidly couple ports 34 and 36 to balloon 32 and delivery or discharge opening 38.

Any of three catheter lengths may be used depending on whether the catheter is introduced into the coronary sinus: (A) through the right atrium or atrial appendage; (B) via the internal jugular or subclavian vein; or (C) via the femoral vein. A guidewire (not shown) is used to facilitate transvenous placement, and a stiffer wire obturator (not shown) is provided for catheter insertion through the right atrial appendage.

Access to the right atrial appendage (approach A) requires an operative approach through the right chest or through the mediastinum. A plegeted pursestring suture (e.g. 4/0 polypropylene), which is conventional in the art, is placed on the right atrium (RA) or atrial appendage, and catheter 30 is secured in place with a Rumel-tourniquet. The transvenous approaches (approaches B and C) require expertise in coronary sinus cannulation over a guidewire using fluoroscopic or echocardiographic guidance. The internal jugular or subclavian approach accesses the coronary sinus via the superior vena cava (SVC) as shown in FIG. 2. The femoral vein approach accesses the coronary sinus via the inferior vena cava (IVC).

After the catheter is placed in the coronary sinus using any of the three approaches described above, the guidewire or obturator, which was used to introduce the catheter into the coronary sinus, is removed. Injection port 36 is then connected to a three-way stopcock (not shown) for intermittent measurement of coronary sinus pressure and administration of the composition(s) provided in accordance with the present invention. With inflation of the low-pressure balloon within the coronary sinus (FIG. 3), a right ventricular pressure wave form is observed. The inventive composition(s) is then administered as a bolus injection through drug injection port 36 so as to be delivered at the delivery port 38. Coronary sinus pressure during bolus injection generally should not exceed about 30 mm Hg. Alternatively, the composition(s) may be administered as a bolus injection followed by continuous infusion or as a continuous infusion alone. Balloon inflation may be rapid inflation/deflation balloon synchronized with the electrocardiogram (ECG). Alternatively, the coronary sinus may be occluded, partially or completely, for a period of about one or two hours. Balloon 32 may have a much thinner wall construction than balloon 42 (discussed below) because it need not expand against arterial pressure. Previously placed pacing leads 12 permit ventricular pacing during drug induced ventricular asystole. Removal of the catheter simply requires deflation of the balloon and closure of the atriotomy with the pursestring suture.

Referring to FIG. 4, another coronary sinus catheter configuration is shown. Catheter 30' is provided with laterally spaced balloons 32' which are fluidly coupled to inflation lumen 39'. Drug delivery lumen 37' opens in a region between the balloons.

Intraventricular Injection

Another drug administration approach is intraventricular injection into the left ventricle via a catheter (not shown). With this approach, the catheter may be delivered in retrograde fashion through the arterial system, aorta and through the aortic valve into the left ventricle. In the alternative, a catheter or cannula may be inserted directly into the left ventricle (preferably the apex) through a hole made by the surgeon. In a further alternative, a needle may be inserted directly into the left ventricle.

Aortic Root Injection

Another drug administration approach is injection of drug into the aortic root with, for example, an intra-aortic delivery catheter 40 as shown in FIG. 5. This permits direct aortic administration of compositions in accordance with the invention during diastole while providing ventricular support analogous to an intra-aortic counterpulsation device. Catheter 40 preferably is a dual lumen catheter provided for rapid inflation and deflation of a durable, low-pressure balloon 42 arranged to inflate in synchronization with heart beat (e.g., electronically synchronized with ECG "P" waves so that balloon 42 inflates during diastole and deflates just before systole). Importantly, complete occlusion of the aorta by the catheter balloon 42 is not required for proper functioning of the device. Thus, risk of injury to the aortic wall, for example, the aortic dissection, is minimized. As in the embodiment discussed above, a balloon inflation port 44 and a drug injection port 46 are provided. Catheter 40 a drug delivery and inflation lumens similar to catheter 30 with the exception that the drug delivery lumen in catheter 40 terminates with a discharge opening 48 proximal to balloon 42 this configuration facilitates delivery of drugs in the vicinity of the coronary arteries. Catheter 40 may be inserted through a hole made by the surgeon in the wall of the aorta as shown in FIG. 5, for example, or endovascularly delivered via a percutaneously catheter insertion in the femoral artery. However, if a catheter is desired to be delivered in a retrograde fashion through the arterial system (e.g. femoral artery and the aorta), the balloon and lumen configuration of catheter 30 or 30', for example, is preferred. The balloon diameter may be larger to correspond with the larger size of the aorta and the balloon walls also may be constructed to withstand the greater pressures in the aorta.

Returning to FIG. 5, which illustrates placement of catheter 40, a pursestring suture (not shown) is placed on the aortic root and catheter 40 is inserted into the ascending aorta and secured with a Rumel tourniquet. The intra-aortic balloon is inflated during diastole and deflated during systole, using the patient's ECO signal for synchronization. Drug delivery is given with a bolus infusion and/or continuous infusion. With drug induced ventricular asystole, the heart is electrically paced, as detailed herein below, permitting continued intra-aortic counterpulsation. In the case of where the accompanying procedure is a coronary artery bypass procedure, catheter 40 is removed after the distal anastomosis is completed. Then, a partially occluding clamp is placed on the aorta, and the aortitomy may be used for the proximal aortosaphenous anastomosis. Alternatively, the catheter 40 may be removed and the aortic pursestring simply tied.

Direct Infusion Into Right Coronary Artery

Another drug administration approach is direct infusion into the right coronary artery (RCA). This approach advantageously delivers drug more local to the AV node than the approaches described above. Other methods are generally less efficient because when mixed in the aorta, ventricle, or other parts of the cardiovascular system, significant drug dilution occurs by the time it reaches the AV branch of the RCA.

This approach can be achieved by either injection into the proximal or ostial portion of the RCA, by use of a guide catheter or drug delivery catheter, or by injection just proximal to the branch perfusing the AV node (AV node artery) by means of a drug delivery catheter positioned in the RCA as shown in FIG. 6. Alternatively, the drug delivery catheter can be positioned directly in the AV node artery through the RCA to delivery the drug more locally to the AV node. The catheter may be introduced into the coronary artery via the arterial system (femoral, radial, subclavian) with a larger diameter coronary guiding catheter. In cases of a left dominant system anatomy or occluded RCA, the catheter may be used in a similar fashion to deliver the drug into the left coronary artery to, for example, the circumflex branch.

Referring to FIG. 6, an exemplary catheter design as shown in the drawings. Catheter 50 is a small diameter (for example, about 3–4 French) single lumen catheter with a drug delivery opening 58 located at the distal end of the catheter to provide selective coronary artery drug delivery. By avoiding the need for a separate channel for balloon inflation, catheter 50 maximizes the volume of catheter lumen dedicated to drug delivery while minimizing catheter diameter.

In use, catheter 50 is introduced into the right coronary artery under flouroscopic guidance through a larger diameter (6–8 French) coronary guiding catheter 56, which is positioned at the ostium, and over a guidewire which is placed distally in the RCA.

After appropriate positioning of the catheter tip, just proximal to or within the take-off of the artery to the atrioventricular node,branch (B) the guiding catheter is pulled back from the ostium of the RCA to provide blood flow to the RCA, the guidewire is removed, and a bolus dose is given. Alternatively, a continuous infusion of drugs can be administered into the distal right coronary artery. Coronary catheter 50 is small enough that blood flow is not significantly impeded to the RCA.

Figure 8:
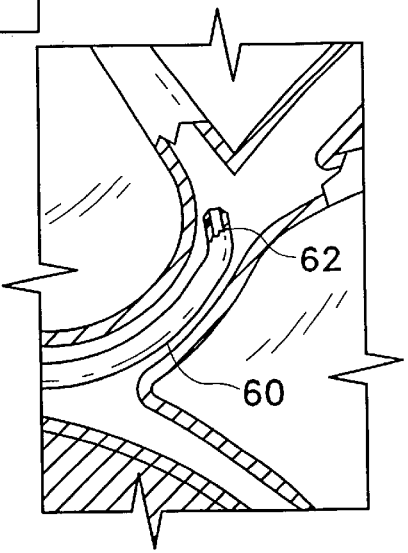
FIG. 8 depicts the catheter of FIG. 7 with its bent distal end portion directed toward the AV node branch.

Referring to FIGS. 7 and 8, another embodiment for the coronary delivery catheter is shown. Catheter 60 is the same as catheter 50 with the exception that catheter 60 has a bent distal end portion 62. Catheter 50 or portion 62 can be positioned within the branch (B) to the AV node. The bent distal end configuration minimizes or eliminates the possibility of the catheter entering the branch going down a posterior left ventricular branch.

Although particular drug administration routes have been described, it should be understood that other routes may be used including, without limitation, needle injection into the aorta, needle injection into the AV node, and trans-epicardial absorption (e.g., a trans-myocardial patch which slowly releases pharmaceutical agents into the myocardium).

Pacing

Prior to drug delivery, the heart is prepared for cardiac pacing as discussed above. In general, leads 12 may be temporarily affixed to the right ventricle of the heart such as by suturing or other manner as would be apparent to one of skill in the art. Drugs are administered to the heart through, for example, any one of catheters 30, 40, 50 or 60 to induce ventricular asystole. Pacing of the heart is established and maintained. The pacing can be transiently interrupted by temporarily deactivating the pacemaker using, for example, foot pedal 22. When the foot pedal is in its deactuated, raised position, the switch in the pacer switch box is closed, and current lows from the ventricular demand pacer 18, through the switch box 14 and the pacing wires 12 to the heart 10 without impediment. During this time, the heart preferably is paced at a rate between 90 to 110 beats/minute. When complete heart block is necessary, to enable a surgical procedure to be performed, pacing is disabled by depressing the foot pedal. In the illustrated and currently preferred embodiment, this opens the switch in pacer switch box 14, stopping the current flow from pacer 18 to pacing leads 12. Since no current reaches the heart while the foot pedal is depressed, ventricular asystole occurs, thus allowing precise suturing or other manipulative procedures to be performed. Once, e.g., a suture has been applied, the pacer may be reactuated by releasing the foot pedal, thereby to reestablish the electrical connection between the pacer 18 and the pacing wires 12 and resuming pacing of the heart at the prescribed rate until another precise manipulation is required. By providing a surgeon-controlled device, such as with a foot pedal, remote from the pacer for controlling the pacer, the surgeon can have complete and immediate control over when pacing is interrupted, even though the surgeon also has surgical instruments in his or her hands. This allows the surgeon to coordinate precisely the pacing of the heart to the manipulative step, thereby minimizing unnecessary and undesired cardiac arrest.

The pacer control box also may be configured to control interruption of a patient's ventilator so that the pacing may be synchronized (e.g., the actuator activates pacing and ventilating equipment (not shown) simultaneously and deactivates pacing and the ventilating equipment simultaneously). Thus, the switch box can be electrically coupled to a ventilator so that when the foot pedal described above is depressed pacing and ventilation are deactivated and when it is released, pacing and ventilation resume. This arrangement may eliminate some small motions of the heart associated with a patient's breathing during a surgical procedure.

The invention will now be described in more detail by reference to the following non-limiting examples.

EXAMPLE 1—In Vivo Studies

The following comparative in vivo studies demonstrated the synergistic effect of the use of the cholinergic agent carbachol in combination with the β-blocker propranolol in stimulating ventricular asystole according to the present invention.

Eleven male crossbred swine weighing 20–25 kg were studied, eight of which received carbachol alone and three of which received carbachol plus propranolol. The swine were sedated using 10 mg/kg IV ketamine. After 20 minutes, the animals were induced with 10 mg/kg IV thiopental sodium and orotracheally intubated. The proper anesthetic plane was maintained with 1% Isoflurane. Periodic arterial blood gas samples were obtained to guide ventilator management. The electrocardiograph was continuously monitored. Through a 7 Fr sheath in the left femoral artery, arterial blood samples were obtained and a micromanometer was inserted to monitor central aortic blood pressure (Millar Instruments, Inc., Houston, Tex.). The heart was exposed through a median sternotomy and suspended in a pericardial cradle. Two temporary epicardial pacing wires were affixed to the right ventricle and connected to an external pacemaker (Medtronic, Inc., Minneapolis, Minn.). The pacemaker was modified to permit deactuation by means of depressing a foot pedal. Through the femoral sheath, an AR-1 guide (Cordis Corp., Miami Lakes, Fla.) was placed into the right coronary artery. An 0.014-inch floppy guide wire was then advanced into the right coronary artery to the level of the posterior descending coronary artery. The AR-1 guide was removed and a 2.5 Fr Tracker (Cordis Corp., Miami Lakes, Fla.) catheter was inserted over the guide wire. Using dye injection, the catheter was positioned just proximal to the take-off of the atrioventricular node artery. Carbachol (Sigma St. Louis, Mo.) solution was prepared the day of the experiment and infused at a constant rate using a Harvard pump.

Animals received either carbachol alone or carbachol in combination with propranolol (Inderal®, Wyeth Ayerst, Philadelphia, Pa.). All animals were instrumented and allowed 10 minutes of hemodynamic stability. Before carbachol was administered, each subject received a 500 ml IV bolus of 0.9% sodium chloride. In the animals receiving carbachol alone, carbachol was continuously infused through the Tracker catheter at increasing doses of 0.44, 0.62, 0.88, and 1.72 mg/min, until ventricular asystole was observed.

In the animals receiving carbachol plus propranolol, a 1 mg dose of propranolol (0.04–0.05 mg/kg) was administered through the Tracker catheter. Carbachol was then administered as a 0.5 mg intracoronary bolus (0.02 mg/kg) followed by a constant infusion. The infusion rate necessary to achieve ventricular asystole was 0.03 mg/min (1.1 to 1.2 μg/kg/min). After carbachol-mediated ventricular asystole was observed, the heart was paced at 100 beats/minute. At 60-second intervals, the pacemaker was turned off for five seconds to determine the underlying cardiac rate and rhythm. The systolic blood pressure (SBP), diastolic blood pressure (DBP), and main arterial pressure (MAP) were recorded every five minutes. The duration of ventricular asystole, defined in this example as a heart rate less than twelve beats per minute, was recorded. Profound hypotension (SBP <60 mmHg) after the administration of carbachol was treated with normal saline, intravenous bolus injections of phenylephrine (0.02 mg/kg), or both. After 75 minutes, the carbachol infusion was stopped and the time required to return to normal sinus rhythm was recorded. The results are set forth in Table 1 below.

TABLE 1

CARBACHOL INTRACORONARY INFUSION

| animal | weight (kg) | infusion rate of carbachol (mg/min) | carbachol dose (μg/kg/min) | duration of ventricular asystole (min) | time to NSR[1] (min) |
|---|---|---|---|---|---|
| 1 | 41 | 0.44 | 10.7 | 76 | |
| 2 | 41 | 0.44 | 10.7 | 75 | |
| 3 | 20 | 0.62 | 31.0 | 47 | |
| 4 | 20 | 1.72 | 86.0 | 87 | |
| 5 | 36 | 0.44 | 12.2 | 75 | 8 |
| 6 | 45 | 0.44 | 9.7 | 53 | |
| 7 | 21 | 0.44 | 20.9 | 24 | |
| 8 | 21 | 0.88 | 41.9 | 76 | 3 |

CARBACHOL AND PROPRANOLOL INTRACORONARY INFUSION

| animal | weight (kg) | infusion rate of carbachol (mg/min) | carbachol dose (μg/kg/min) | duration of ventricular asystole (min) | time to NSR (min) |
|---|---|---|---|---|---|
| 1 | 25 | 0.03 | 1.2 | 75 | 5 |
| 2 | 27 | 0.03 | 1.1 | 75 | 7 |
| 3 | 26 | 0.03 | 1.2 | 63 | 15 |

[1]NSR = normal sinus rhythm. Blank entries indicate data not recorded.

EXAMPLE 2—Treatment of Human Patients

Ten human patients were treated pursuant to an investigational new drug clinical trial following Institutional Review Board and FDA approval and informed consent.

Repair of a leaky distal anastomosis was performed on 9 human patients (designated Patients 101–109) with stable coronary artery disease (CAD) following open-chest coronary artery bypass graft (CABG) surgery. The study was conducted to assess the ability to induce pacemaker-dependent reversible ventricular asystole in patients on cardiopulmonary bypass (CPB) utilizing an aortic cross clamp undergoing an open-chest CABG procedure. Established institutional techniques for preparation and conduct of CABG were used. At the end of the surgical procedure, and after the aortic cross clamp was removed, the AV-node blocker carbachol and the beta-blocker propranolol were serially administered to the patients to induce pacemaker-dependent ventricular asystole. In Patients 101–109, the propranolol and carbachol were used at the end of the CABG surgery only during repair of leaking distal vascular anastomoses, while the patients were still on cardiopulmonary bypass (CPB) subsequent to the removal of the aortic cross clamp. In the tenth patient (designated Patient 201), the carbachol and propranolol drugs and temporary pacing were used for the CABG procedure itself, and the aortic cross clamp was avoided.

The patients were selected based on the following key criteria. Patients were selected ranging between 18 and 70 years in age with a normal sinus rhythm with P-wave-R- wave interval not exceeding 0.16 sec. Men or women were selected who had a stable coronary artery disease and were undergoing elective CABG revascularization of distal target (s) in the left anterior descending (LAD) artery system, right coronary artery (RCA) and/or the left circumflex (LCX) artery. Patients were selected with right dominant coronary circulation or an expectation that their AV node was supplied by the RCA, and with the presence of at least two of the following angiographic criteria: (1) coronary arteries greater than 2 mm in diameter, (2) noncalcified coronary arteries, or (3) an LAD that was not intramyocardial.

Patients with any of the following conditions were intended to be excluded from the study: (1) significant left main coronary artery stenosis, (2) left dominant coronary circulation, (3) RCA with proximal chronic total occlusion or inability to pass drug infusion catheter past proximal RCA stenosis, (4) presence of any significant hemodynamic instability, including, but not limited to, unstable angina or active ischemia requiring maximal medical management, malignant ventricular arrhythmias currently requiring medical management or cardiogenic shock requiring blood pressure support, (5) presence of any significant condition that increases the risk of the CABG procedure or other study procedure, including but not limited to, a history of peripheral vascular disease, hypertensive heart disease, cardiomyopathy, New York Health Association (NYHA) Class 3 or 4 congestive heart failure, chronic renal insufficiency or failure, prior CAB G, valvular heart disease, unusual body habitus (e.g., morbid obesity), presence of acute pulmonary infection/pneumonia, metastatic cancer, thyrotoxicosis, sepsis, history of stroke or transient ischemic attack (TIA) or asymptomatic carotid bruit, (6) recent (within 2 weeks) acute myocardial infarction, (7) documented cardiac ejection fraction <30% within 30 days of planned procedure, (8) presence of any significant condition that would make the determination of the efficacy and/or safety endpoints of the study more difficult, including, but not limited to, first or second degree heart block, left or right bundle branch block or other IVCD, (9) presence of any significant condition that increases the risk of exposure to any of the components of the drugs as follows: Propranolol—This includes, but is not limited to, significant asthma, obstructive lung disease, congestive heart failure, hypersensitivity to propranolol or other beta-adrenergic antagonists; Carbachol—This includes, but is not limited to, asthma, obstructive lung disease, epilepsy, Parkinsonism, peptic ulcer disease, hepatic insufficiency, hypersensitivity to carbachol or other cholinergic agonists (i.e., cholinomimetics or acetyl-cholinesterase inhibitors), (10) presence of any significant condition that increases the risk of use of a temporary pacemaker. This includes, but is not limited to, implanted permanent pacemaker, history of ventricular tachycardia or fibrillation requiring current antiarrhythmic therapy, other arrhythmia or condition that increases the risk of cardiac pacing, e.g., Wolfe-Parkinson-White syndrome, and (11) pregnant or nursing women.

For Patients 101–109, CABG surgery was performed using well established traditional methods. Patients were placed on CPB, the aorta was cross-clamped and cardioplegic arrest was administered. After distal and (if applicable) proximal anastomoses were sutured, the cross-clamp was removed and (if necessary) the heart defibrillated with patients still on CPB. When a leak requiring repair was detected at the distal anastomotic site(s), epicardial pacemaker leads were sewn into place on the ventricles and, optionally, the right atrium, of the patients and the pacing thresholds determined and recorded. A temporary pacemaker was connected to the epicardial leads. The pacing voltage was set at 10 times the pacing threshold. The pacemaker was first placed in ventricular-ventricular inhibited (VVI) mode with a rate of 60±15 bpm and pacing ensued for 2 minutes. Hemodynamic acceptability of the VVI-paced rhythm was assessed. The pacemaker was then set in ventricular-atrial triggered (VAT) mode and pacing ensued for another 2 minutes. Hemodynamic acceptability of the VAT-paced rhythm was assessed.

During surgery and prior to administration of the drug protocol, fluoroscopy was used to position an appropriate catheter, e.g., a Tracker™ (Target Therapeutics, Freemont, Calif.) catheter with an appropriate guide wire, in the proximal right coronary artery. This catheter was used for intracoronary administration of the study drugs. If at any time during the procedure, catheter displacement was noted, repeat angiography was used to reposition the catheter. Adequate supplies of phenylephrine, other adrenergic agents and volume repletion fluids were available at the bedside during and following drug administration in the event of unexpected adverse events, to control blood pressure, and/or to protect against inadvertent overdose.

The propranolol solution used was an injectable solution of Inderal® (Wyeth-Ayerst, Philadelphia, Pa.). The initial propranolol dose was 1 mg of a 1 mg/mL solution. Carbachol was provided in a vial containing 6 mL of a 0.255% solution (mg/dL). Each vial contained 2.55 mg/ml of carbachol in 5 mM sodium citrate and was adjusted to pH=7.0 using citric acid. The carbachol infusion solution was prepared by adding 5 mL of this solution to 250 mL of sterile saline. After reconstitution, the resulting concentration of the carbachol solution was 0.005%, or 0.05 mg/mL. The initial dose of carbachol was 0.025 mg or 0.5 mL and the initial infusion rate was 0.025 mg/min or 0.5 mL/min of the 0.005% solution.

A loading dose of propranolol ranging between 1–6 mg first was given to patients over a period of 1–3 minutes. Carbachol was administered as an intracoronary low dose bolus and as an infusion. For Patients 101–108, the bolus dose of carbachol used to initiate reversible ventricular asystole was in the range of 0.05–0.225 mg and the sustained infusion of carbachol used to maintain ventricular asystole was in the range of 0.05–0.15 mg/min. In one of the patients studied, overdrive pacing was used in conjunction with the loading dose of carbachol to induce ventricular asystole. Once complete heart block was achieved with no ventricular escape beats, and a pacemaker-dependent rhythm established, for patients 101–108 the distal anastomosis(es) were repaired during brief (up to 5 seconds) interruptions of pacing.

For Patient 201, the drugs and temporary pacing were used for the CABG procedure itself. A loading dose of 4 mg propranolol and 0.15 mg of carbachol were administered via intracoronary delivery to Patient 201 to initiate reversible ventricular asystole. Subsequently, an infusion of carbachol at a rate of 0.1 mg/min was given via intracoronary delivery to the patient to maintain ventricular asytole for a period of about 45 minutes. During this arrest period, a left internal mammary artery and obtuse marginal graft procedure were performed by the surgeon using intermittent pacing interruptions to successfully place the distal graft anastamosis sutures on a substantially still rather than moving heart, producing the benefit of an improved technical result and avoidance of cross-clamping of the aorta.

A dose of phenylephrine ranging between about 0.24–0.80 mg was administered to Patients 101, 103, 105–109 and 201 to control hypotension. When a satisfactory technical result had been achieved, the drug infusion was stopped and atropine was administered to determine the reliability of pharmacologic reversal of complete heart block with the exception of Patient 201, who was allowed to return to normal sinus rhythm naturally, over less than 15 minutes. The dosage amount of atropine used to reverse arrest in Patients 101–108 was about 1.0 mg. At the close of the pharmacologic protocol, after resumption of normal A-V conduction, CPB was removed. Established procedures for closing of the chest were followed.

In one patient, Patient 109, no arrest was achieved, however retrospective review of the post-operative angiogram revealed that the patient was a left dominant patient, ie., having the AV node fed from the left coronary artery rather than the right coronary artery, where the catheter was placed. Transesophageal echocardiography (TEE) revealed normal left and right ventricular function, i.e., with no reported global or regional wall motion abnormalities in each patient in which arrest was achieved.

The results are shown in Table 2 below.

TABLE 2

| Patient | Minutes of Arrest | Propranol total dose- mg | Carbachol bolus - total mg | Carbachol Infusion mg/min | Arrest | Hypotension-phenylephrine used |
|---|---|---|---|---|---|---|
| 101 | 7 | 3 | 0.15 | 0.10 | Yes | Yes |
| 102 | 13 | 1 | 0.05 | 0.05 | Yes | No |
| 103 | 10 | 2 | 0.075 | 0.05 | Yes | Yes |
| 104 | 4 | 3 | 0.225 | 0.1 | Yes | No |
| 105 | 8 | 2 | 0.075 | 0.075 | Yes | Yes |
| 106 | 12 | 3 | 0.1 | 0.075 | Yes | Yes |
| 107 | 5 | 4 | 0.125 | 0.15 | Yes | Yes |
| 108 | 2 | 3 | 0.2 | 0.1 | Yes | Yes |
| 109 |  | 6 | 0.5 | 0.125 | No | Yes |
| 201 | 45 | 4 | 0.15 | 0.1 | Yes | Yes |

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

What is claimed is:

1. A method of performing a medical procedure on a human patient comprising:
    placing the patient on cardiopulmonary bypass support;
    administering at least a first agent to the heart of the patient which is capable of inducing at least one period of reversible ventricular asystole of the heart, while maintaining the ability of the heart to be electrically paced; and
    performing at least one step of the medical procedure during the at least one period of ventricular asystole; said method further comprising electrically pacing the heart at least once during the medical procedure.

2. The method of claim 1 wherein the at least one period of ventricular asystole has a duration of between about 30 to 90 minutes.

3. The method of claim 2 wherein the at least one period of ventricular asystole has a duration of between about 30 to 45 minutes.

4. The method of claim 1 wherein the administration of at least a first agent to the heart of the patient comprises administering an AV node blocker to the heart at a sufficient dosage amount to induce at least one period of reversible ventricular asystole of the heart.

5. The method of claim 4 further comprising administering a β-blocker to the patient.

6. The method of claim 5 wherein the β-blocker is administered to the heart of the patient.

7. The method of claim 4 wherein the AV node blocker comprises a cholinergic receptor agonist.

8. The method of claim 7 wherein the cholinergic receptor agonist comprises carbachol.

9. The method of claim 8 wherein the carbachol is administered in an amount of about 0.1 to 4.8 μg/kg body weight/min.

10. The method of claim 5 wherein the β-blocker comprises propranolol.

11. The method of claim 10, wherein the propranolol is administered in an amount of about 0.01 to 0.07 mg/kg body weight.

12. The method of claim 6 wherein the β-blocker is administered prior to the AV node blocker.

13. The method of claim 6 wherein the β-blocker is administered in an amount sufficient to substantially reduce the amount of AV node blocker required to induce asystole of the heart.

14. The method of claim 6 wherein the AV node blocker and the β-blocker are administered to the right or left coronary artery of the heart.

15. The method of claim 14 wherein the AV node blocker and the β-blocker are administered to the right or left coronary artery through a drug delivery catheter which has at least one outlet which is positioned in the right or left coronary artery.

16. The method of claim 15 wherein the outlet is positioned in the right coronary artery proximate to the AV node artery.

17. The method of claim 15 wherein the drug delivery catheter is percutaneously inserted into the right coronary artery from a peripheral vascular access point.

18. The method of claim 17 wherein the peripheral vascular access point is a femoral artery.

19. The method of claim 17 wherein the peripheral vascular access point is a radial artery.

20. The method of claim 1 wherein the agent is delivered by needle injection into a coronary vessel.

21. The method of claim 1 wherein the medical procedure is a coronary artery bypass graft procedure.

22. The method of claim 21, wherein the coronary artery bypass graft procedure avoids the use of an aortic cross-clamp.

23. The method of claim 1 wherein the medical procedure is a valve procedure.

* * * * *